(12) United States Patent
Liew et al.

(10) Patent No.: US 10,294,498 B2
(45) Date of Patent: May 21, 2019

(54) MICROORGANISM WITH MODIFIED ALDEHYDE:FERREDOXIN OXIDOREDUCTASE ACTIVITY AND RELATED METHODS

(71) Applicant: LanzaTech, Inc., Skokie, IL (US)

(72) Inventors: Fungmin Liew, Skokie, IL (US); Michael Koepke, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

(21) Appl. No.: 15/594,252

(22) Filed: May 12, 2017

(65) Prior Publication Data

US 2017/0327849 A1    Nov. 16, 2017

Related U.S. Application Data

(60) Provisional application No. 62/336,639, filed on May 14, 2016.

(51) Int. Cl.
| | | |
|---|---|---|
| C12N 1/20 | (2006.01) | |
| C12P 7/06 | (2006.01) | |
| C12P 7/64 | (2006.01) | |
| C12P 5/00 | (2006.01) | |
| C12P 5/02 | (2006.01) | |

(52) U.S. Cl.
CPC .......... C12P 7/065 (2013.01); C12N 1/20 (2013.01); C12P 5/007 (2013.01); C12P 5/026 (2013.01); C12P 7/6436 (2013.01); C12Y 101/01001 (2013.01); C12Y 102/0101 (2013.01); C12Y 102/07005 (2013.01); Y02E 50/17 (2013.01)

(58) Field of Classification Search
None
See application file for complete search history.

(56) References Cited

U.S. PATENT DOCUMENTS

| | | | |
|---|---|---|---|
| 2010/0151543 | A1 | 6/2010 | Reeves |
| 2011/0262954 | A1* | 10/2011 | Thomm .............. C12N 15/1086 435/29 |
| 2015/0079650 | A1 | 3/2015 | Koepke et al. |
| 2015/0275238 | A1* | 10/2015 | Kelly .................... C12P 7/22 435/156 |

(Continued)

OTHER PUBLICATIONS

Basen et al., "Single gene insertion drives bioalcohol production by a thermophilic archaeon", Proceedings of the National Academy of Sciences USA, vol. 111, No. 49, pp. 17618-17623, 2014.*

(Continued)

*Primary Examiner* — Richard C Ekstrom
(74) *Attorney, Agent, or Firm* — Andrea Schoen

(57) ABSTRACT

The invention provides a non-naturally occurring bacterium having decreased or eliminated activity of an enzyme that catalyzes the reaction defined by EC 1.2.7.5, such as aldehyde:ferredoxin oxidoreductase (AOR). Optionally, the bacterium also has decreased or eliminated activity of an enzyme that catalyzes the reaction defined by EC 1.2.1.10 and/or EC 1.1.1.1, such as aldehyde dehydrogenase, alcohol dehydrogenase, or bifunctional aldehyde/alcohol dehydrogenase. The invention further provides methods of producing products by culturing the bacterium in the presence of a gaseous substrate containing one or more of CO, $CO_2$, and $H_2$.

13 Claims, 17 Drawing Sheets

(56) References Cited

U.S. PATENT DOCUMENTS

2017/0327849 A1* 11/2017 Liew .................. C12P 7/065

OTHER PUBLICATIONS

Keller et al., "Ethanol production by the hyperthermophilic archaeon Pyrococcus furiosus by expression of bacterial bifunctional alcohol dehydrogenases", Microbial Biotechnology, vol. 10, pp. 1535-1545, 2017.*
Nguyen et al., "Temperature-dependent acetoin production by Pyrococcus furiosis is catalyzed by a biosynthetic acetolactate synthase and its deletion improves ethanol production", Metabolic Engineering, vol. 34, pp. 71-79, 2016.*
Liew et al., "Metabolic engineering of Clostridium autoethanogenum for selective alcohol production", Metabolic Engineering, vol. 40, pp. 104-114, 2017.*
Basen, PNAS USA, 111: 17618-17623, 2014.
Brown, Biotechnol Biofuels, 7: 1-18, 2014.
Drake, Ann NY Acad Sci, 1125: 100-128, 2008.
Fast, Curr Opin Chem Eng, 1: 380-395, 2012.
Heider, J Bacteriol, 177: 4757-4764, 1995.
Köpke, Curr Opin Biotechnol 22: 320-325, 2011.
Köpke, PNAS USA, 107: 13087-13092, 2010.
Leang, Appl Environ Microbiol, 79: 1102-1109, 2013.
Membrillo-Hernandez, J Bacteriol, 181: 7571-7579, 1999.
Mock, J Bacteriol, 197: 2965-2980, 2015.
Wang, J Bacteriol, 195: 4373-4386, 2013.

* cited by examiner

MICROORGANISM WITH MODIFIED ALDEHYDE:FERREDOXIN OXIDOREDUCTASE ACTIVITY AND RELATED METHODS

CROSS REFERENCE TO RELATED APPLICATIONS

This application claims the benefit of U.S. Provisional Patent Application 62/336,639 filed May 14, 2016, the entirety of which is incorporated herein by reference.

BACKGROUND OF THE INVENTION

The deleterious environmental impact caused by the continuing extraction and exploitation of fossil fuels for energy and chemicals, coupled with their inherent finite nature, are the principle drivers for the development of sustainable alternatives. In this regard, gas fermentation has emerged as a promising technology for the biological conversion of industrial waste gases into fuels and chemicals. However, only a limited suite of products have been produced via gas fermentation to date, largely due to the lack of genetic tools and enzymatic pathways presently developed for gas-fermenting bacteria. Accordingly, there remains a need for alternative microorganisms and methods for the production of fuels and chemicals.

SUMMARY OF THE INVENTION

The invention provides a non-naturally occurring bacterium having decreased or eliminated activity of an enzyme that catalyzes the reaction defined by EC 1.2.7.5 compared to a parental bacterium. Generally, the non-naturally occurring bacterium comprises at least one disruptive mutation in a gene encoding the enzyme that catalyzes the reaction defined by EC 1.2.7.5. In a preferred embodiment, the enzyme that catalyzes the reaction defined by EC 1.2.7.5 is aldehyde:ferredoxin oxidoreductase (AOR).

Sometimes, the non-naturally occurring bacterium further has decreased or eliminated activity of at least one enzyme that catalyzes the reaction defined by EC 1.2.1.10 and/or EC 1.1.1.1 compared to the parental bacterium, such as at least one disruptive mutation in a gene encoding the enzyme that catalyzes the reaction defined by EC 1.2.1.10 and/or EC 1.1.1.1. The enzyme that catalyzes the reaction defined by EC 1.2.1.10 and/or EC 1.1.1.1 is preferably selected from the group consisting of bifunctional aldehyde/alcohol dehydrogenase, aldehyde dehydrogenase, and alcohol dehydrogenase.

These genetic modifications render the non-naturally bacterium suitable for producing products such as acetyl-CoA, acetoacetyl-CoA, acetoacetate, acetone, isopropanol, 3-hydroxyisovaleryl-CoA, 3-hydroxyisovalerate, isobutylene, isoprene, 3-hydroxybutyryl-CoA, 3-hydroxybutyrate, 3-hydroxybutyrylaldehyde, 1,3-butanediol, 2-hydroxyisobutyryl-CoA, 2-hydroxyisobutyrate, pyruvate, acetolactate, acetoin, 2,3-butanediol, and lactate.

In certain embodiments, the non-naturally occurring bacterium is a C1-fixing bacterium, such as a bacterium that consumes a gaseous substrate comprising one or more of $CO$, $CO_2$, and $H_2$.

The non-naturally occurring bacterium is typically derived from a parental bacterium that comprises an enzyme that catalyzes the reaction defined by EC 1.2.7.5, such as *Alkalibaculum bacchi*, *Blautia product*, *Butyribacterium methylotrophicum*, *Chloroflexus aurantiacus*, *Clostridium aceticum*, *Clostridium acetobutylicum*, *Clostridium autoethanogenum*, *Clostridium botulinum*, *Clostridium carboxidivorans*, *Clostridium coskatii*, *Clostridium drakei*, *Clostridium formicoaceticum*, *Clostridium ljungdahlii*, *Clostridium ragsdalei*, *Desulfovibrio vulgaris*, *Eubacterium limosum*, *Geobacter sulfurreducens*, *Methylomicrobium alcaliphilum*, *Moorella thermoautrophica*, *Moorella thermoacetica*, *Rhodospirillum rubrum*, *Sporomusa ovata*, *Sporomusa silvacetica*, *Sporomusa sphaeroides*, *Thermanaerovibrio acidaminovorans*, *Thermanaerovibrio acidaminovorans*, *Thermoanaerobacter wiegelii*, *Thermodesulfovibrio yellowstonii*, *Thermodesulfovibrio yellowstonii*, or *Thermus thermophilus*.

The invention further provides a method of producing a product by culturing such a non-naturally occurring bacterium. This culturing may be performed in the presence of a gaseous substrate comprising one or more of $CO$, $CO_2$, and $H_2$.

*nogenum* WT genomic DNA control; 2-5, 8-11, 14-17=clones of aor double KO strain with restored pyrE; 19-22=HindIII digested genomic DNA of aor1 KO strain.

Figure 5:
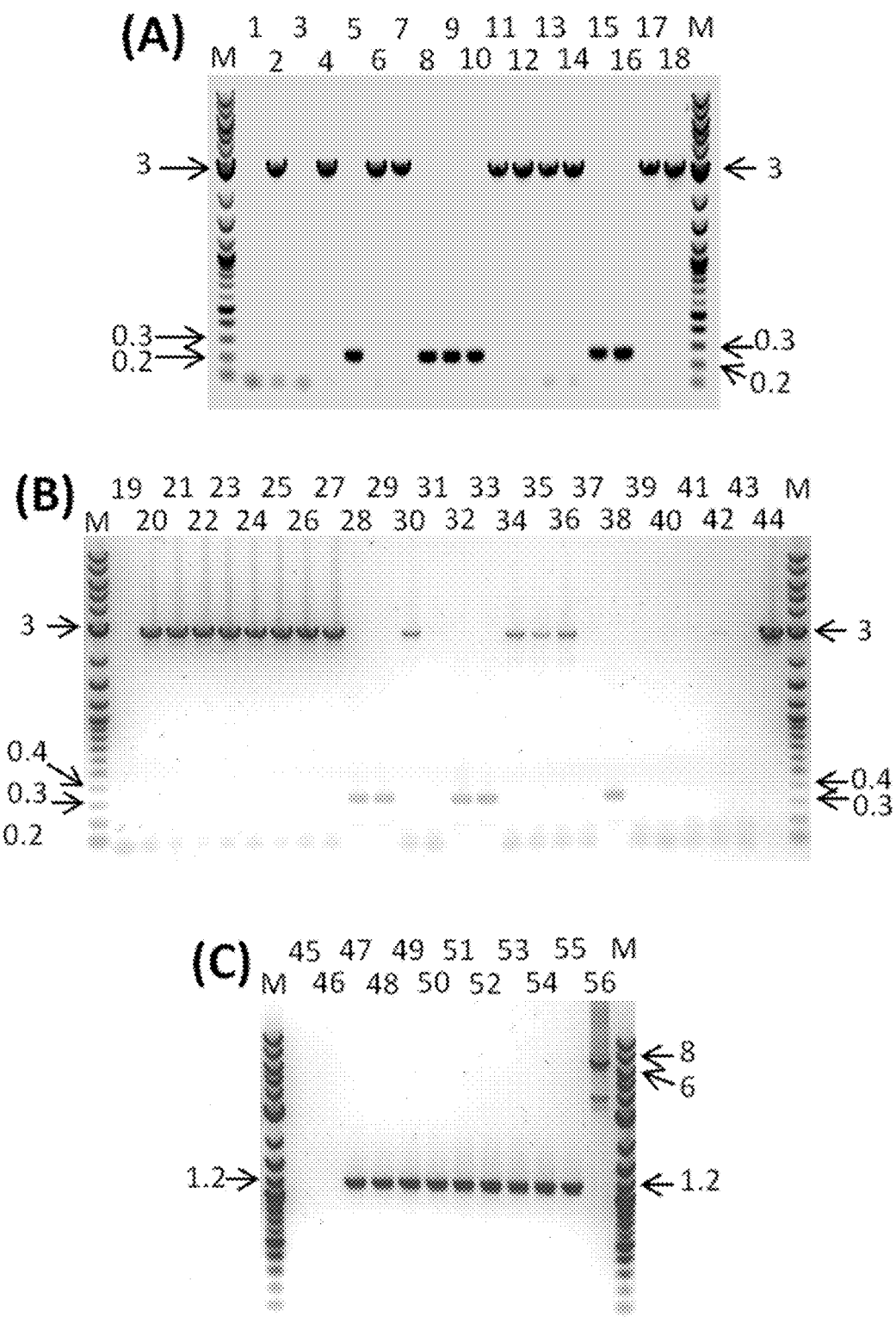

FIG. 5 is a set of gel images showing screening of *C. autoethanogenum* ΔadhE1mut, ΔadhE1 and ΔadhE1+2 strains. (A) PCR screening of ΔadhE1mut strains; (B) PCR screening of ΔadhE1 strains; and (C) PCR screening of ΔadhE1+2 strains. Lanes 5, 8, 9, 10, 15 & 16=ΔadhE1mut strains; Lanes 28, 29, 32, 33 & 38=ΔadhE1 strains; Lanes 47-55=ΔadhE1+2 strains; Lanes 1, 19 & 45=non-template controls; Lanes 18, 44 & 56=WT genomic DNA control; M=NEB 2-log DNA ladder in kb.

Figure 6:
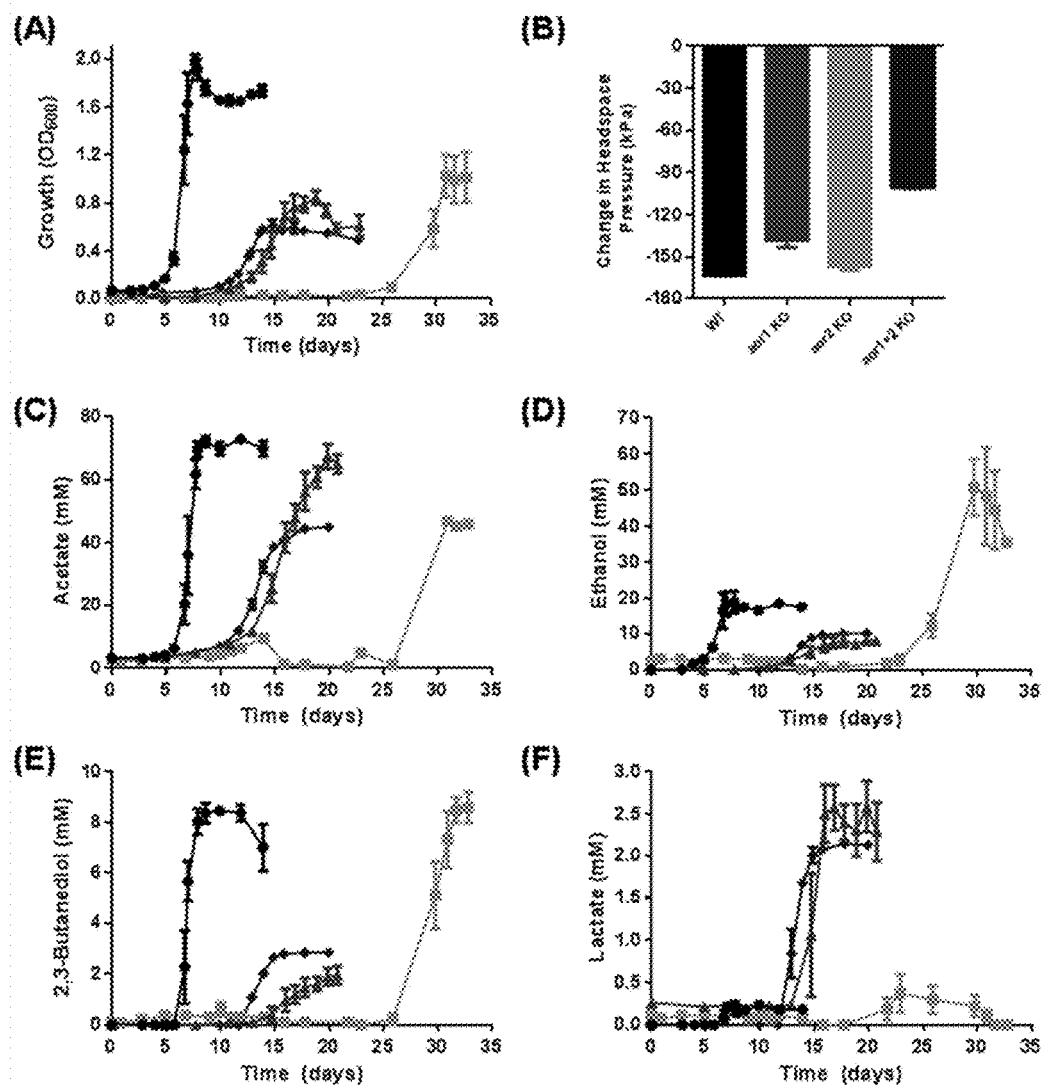

FIG. 6 is a set of graphs showing growth, headspace pressure change and metabolite profiles of *C. autoethanogenum* WT (circles), aor1 KO (triangles), aor2 KO (squares), and aor1+2 KO strains (diamonds) on CO. (A) Growth profile; (B) Change in headspace pressure from start to end of cultivation; (C) Acetate profile; (D) Ethanol profile; (E) 2,3-Butanediol profile; and (F) Lactate profile; For each strain n=4, except for aor2 KO n=3; Error bars=s.e.m.

Figure 7:
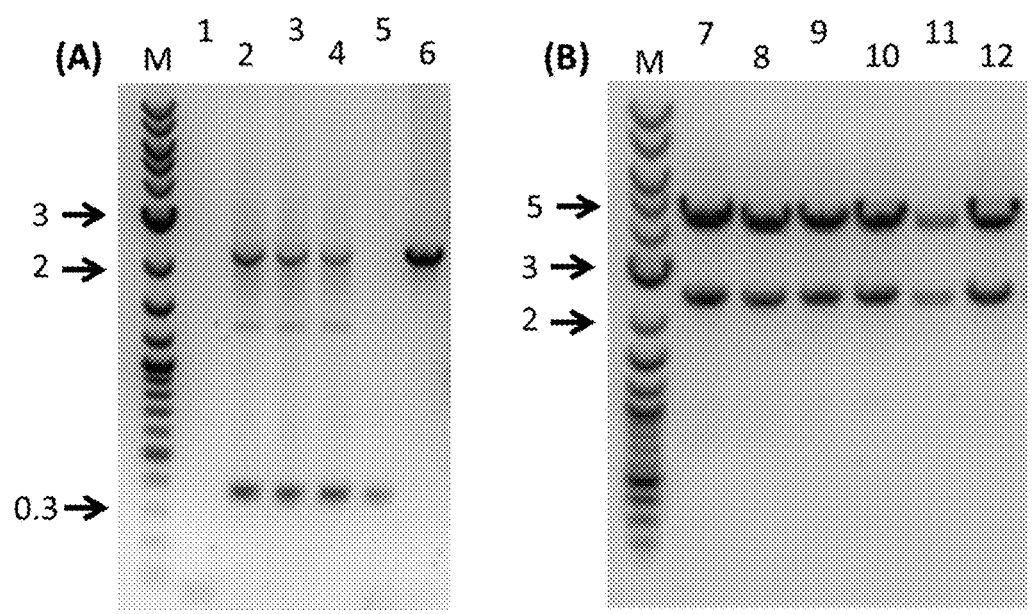

FIG. 7 is a set of gel images showing verification of complemented aor1 strain. (A) PCR of genomic DNA from aor1 complemented aor1 strain (lanes 2-4) using exon spanning aor1 primers; M=NEB 2-Log DNA ladder; 1=non-template control; 5=WT genomic DNA control; 6=aor1 KO control; (B) AscI and PmeI restriction digests of rescued plasmids pMTL83151-PacsA-aor1 from complemented strain (lanes 7-12).

Figure 8:
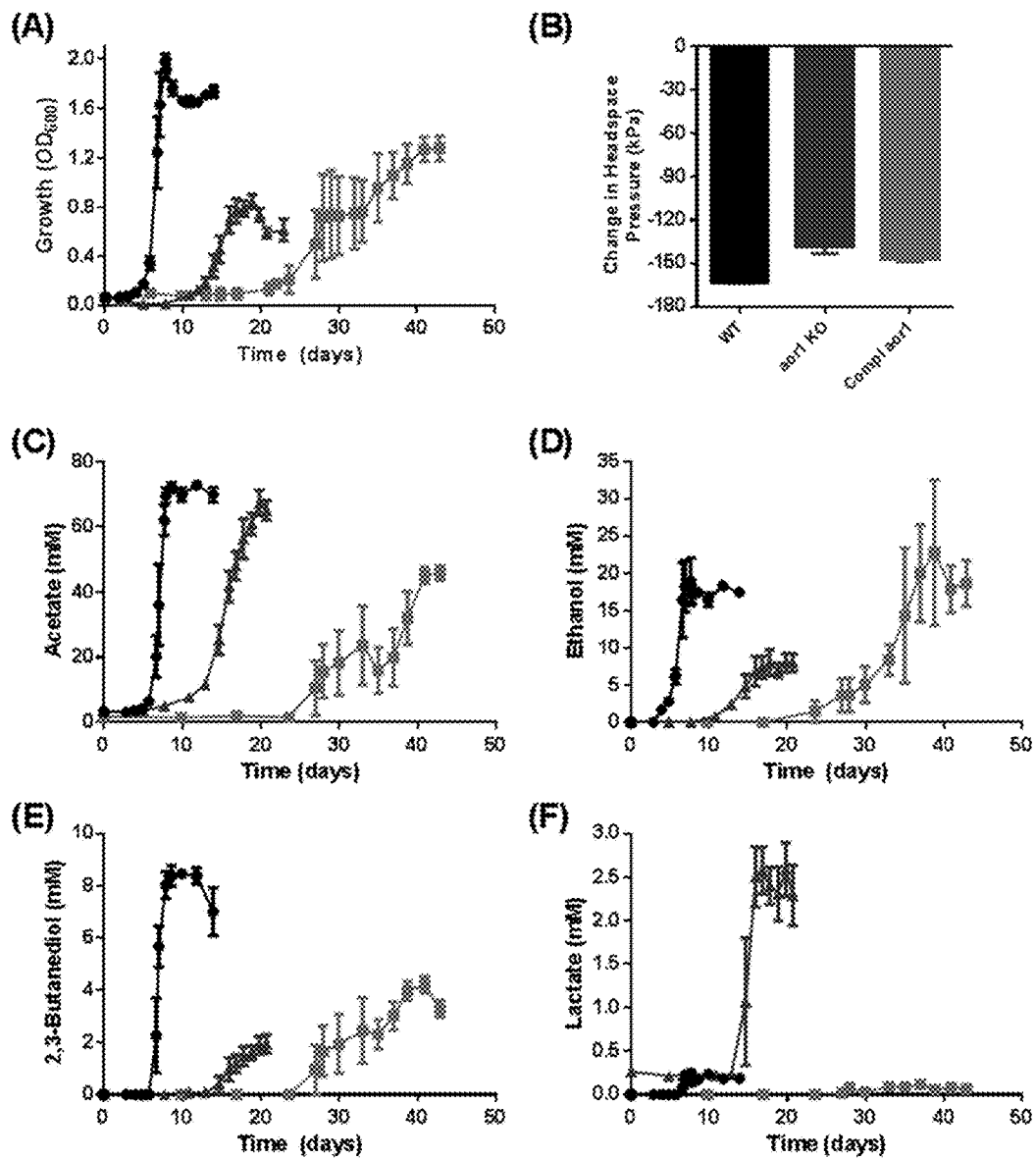

FIG. 8 is a set of graphs showing growth, headspace pressure, and metabolite profiles of *C. autoethanogenum* WT, aor1 KO, and complemented aor1 strains on 200 kPa CO. (A) Growth profile; (B) Change in headspace pressure (C) Acetate profile; (D) Ethanol profile; (E) 2,3-Butanediol profile; and (F) Lactate profile. Circles=WT (n=4); Triangles=aor1 strains (n=4); Squares=complemented aor1 strains (n=3); Error bars=standard error of mean.

Figure 9:
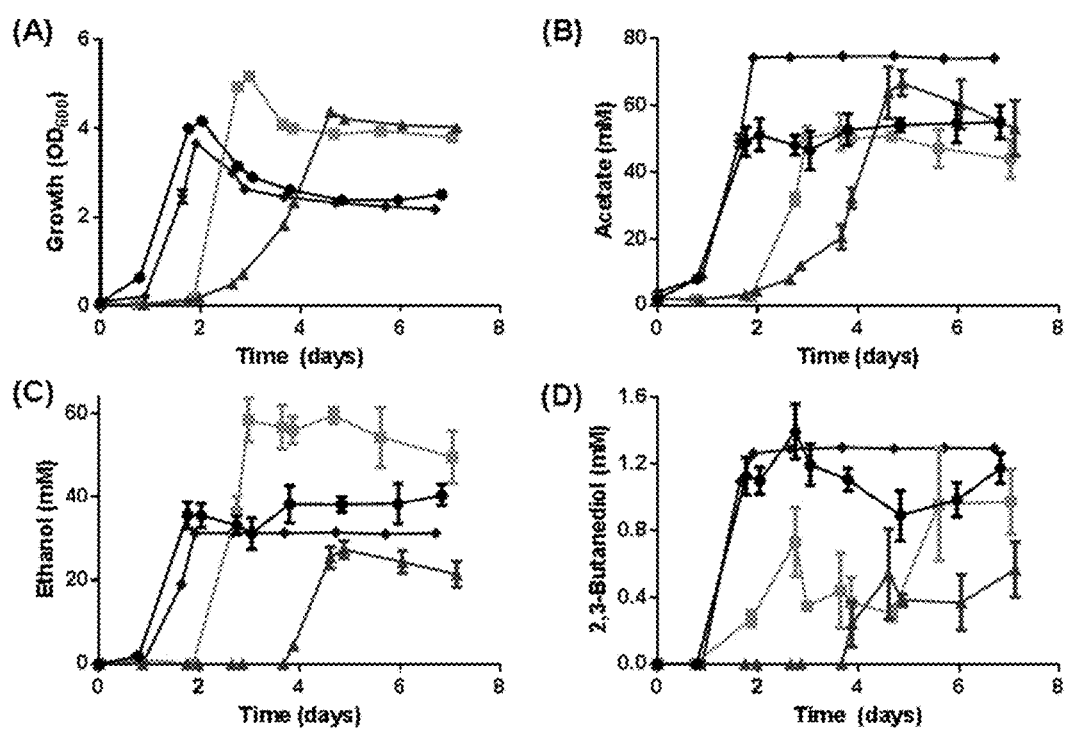

FIG. 9 is a set of graphs showing growth and metabolite profiles of *C. autoethanogenum* WT, aor1 KO, aor2 KO and aor1+2 KO strains on fructose. (A) Growth profile; (B) Acetate profile; (C) Ethanol profile; and (D) 2,3-Butanediol profile. Circles=WT (n=4); Triangles=aor1 strain (n=3); Squares=aor2 strain (n=3); Diamonds=aor1+2 KO strain (n=4); Error bars=s.e.m.

Figure 10:
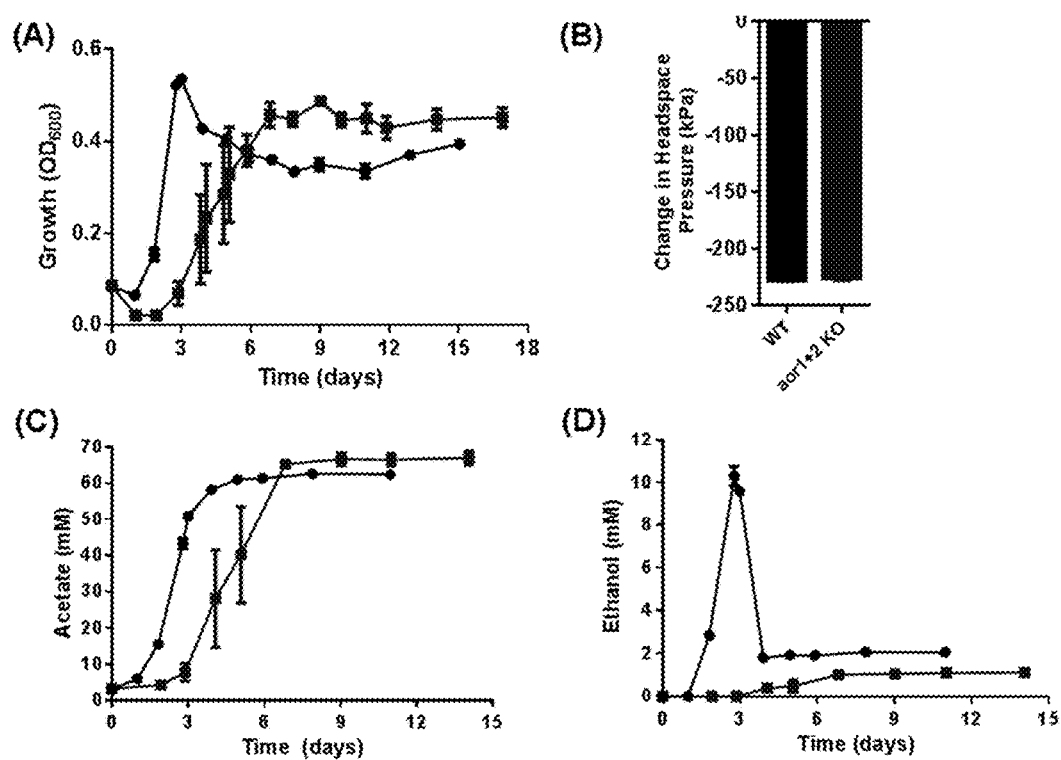

FIG. 10 is a set of graphs showing growth, headspace pressure, and metabolite profiles of *C. autoethanogenum* WT, and aor1+2 KO strain on $H_2+CO_2$. (A) Growth profile; (B) Change in headspace pressure (C) Acetate profile; (D) Ethanol profile; Circles=WT (n=4); Squares=aor1+2 KO strain (n=4); Error bars=s.e.m.

Figure 11:
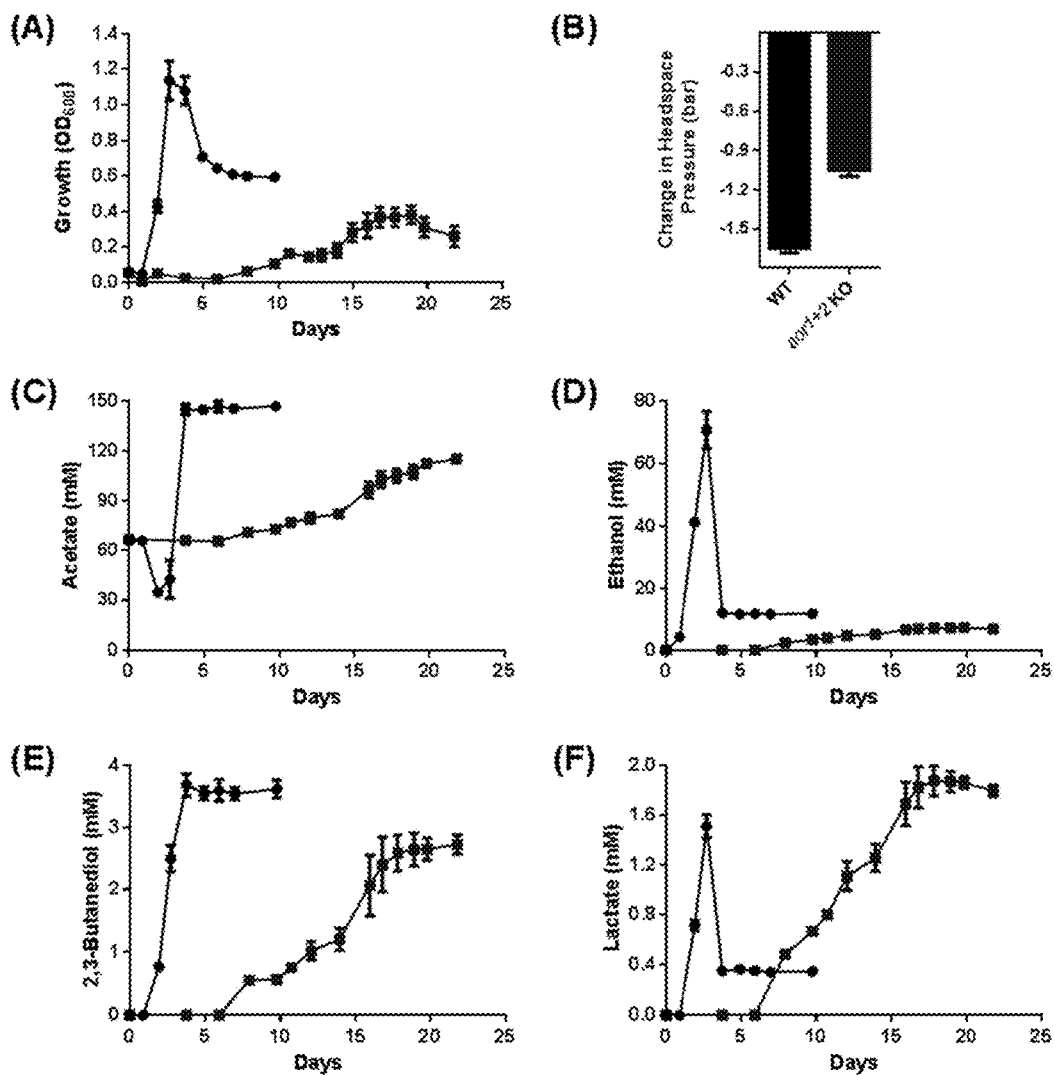

FIG. 11 is a set of graphs showing growth, headspace pressure, and metabolite profiles of *C. autoethanogenum* WT and aor1+2 KO strain t in the presence of 60 mM acetate and 200 kPa CO. (A) Growth profile; (B) Change in headspace pressure; (C) Acetate profile; (D) Ethanol profile; (E) 2,3-Butanediol profile; and (F) Lactate profile. Circles=WT; Squares=aor1+2 KO strain; n=3; Error bars=s.e.m.

Figure 12:
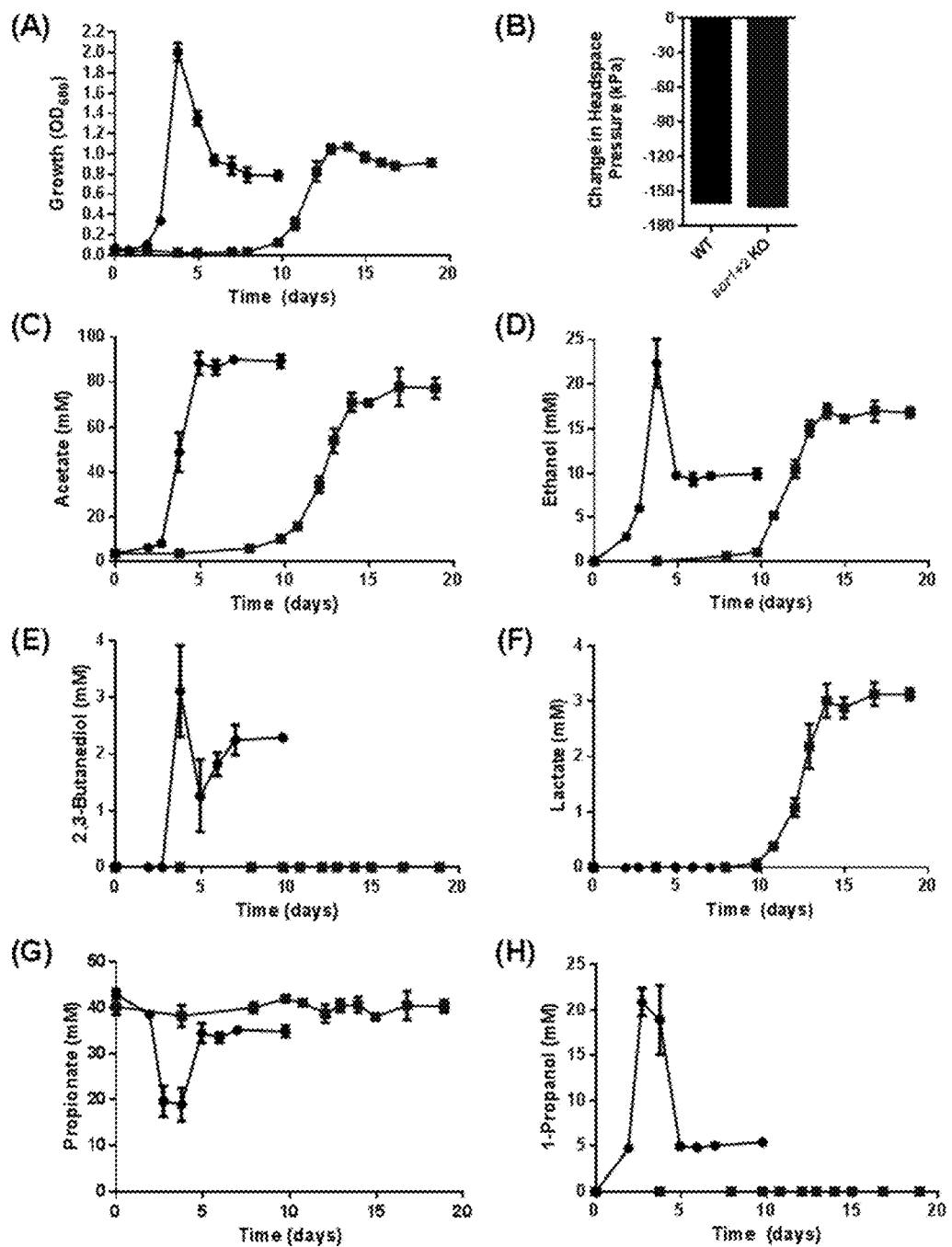

FIG. 12 is a set of graphs showing growth, headspace pressure and metabolite profiles of *C. autoethanogenum* WT and aor1+2 KO strain in the presence of 40 mM propionate and 200 kPa CO. (A) Growth profile; (B) Change in headspace pressure; (C) Acetate profile; (D) Ethanol profile; (E) 2,3-Butanediol profile; (F) Lactate profile; (G) Propionate profile; and (H) 1-Propanol profile. Circles=WT; Squares=aor1+2 KO strain; n=3; Error bars=s.e.m.

Figure 13:
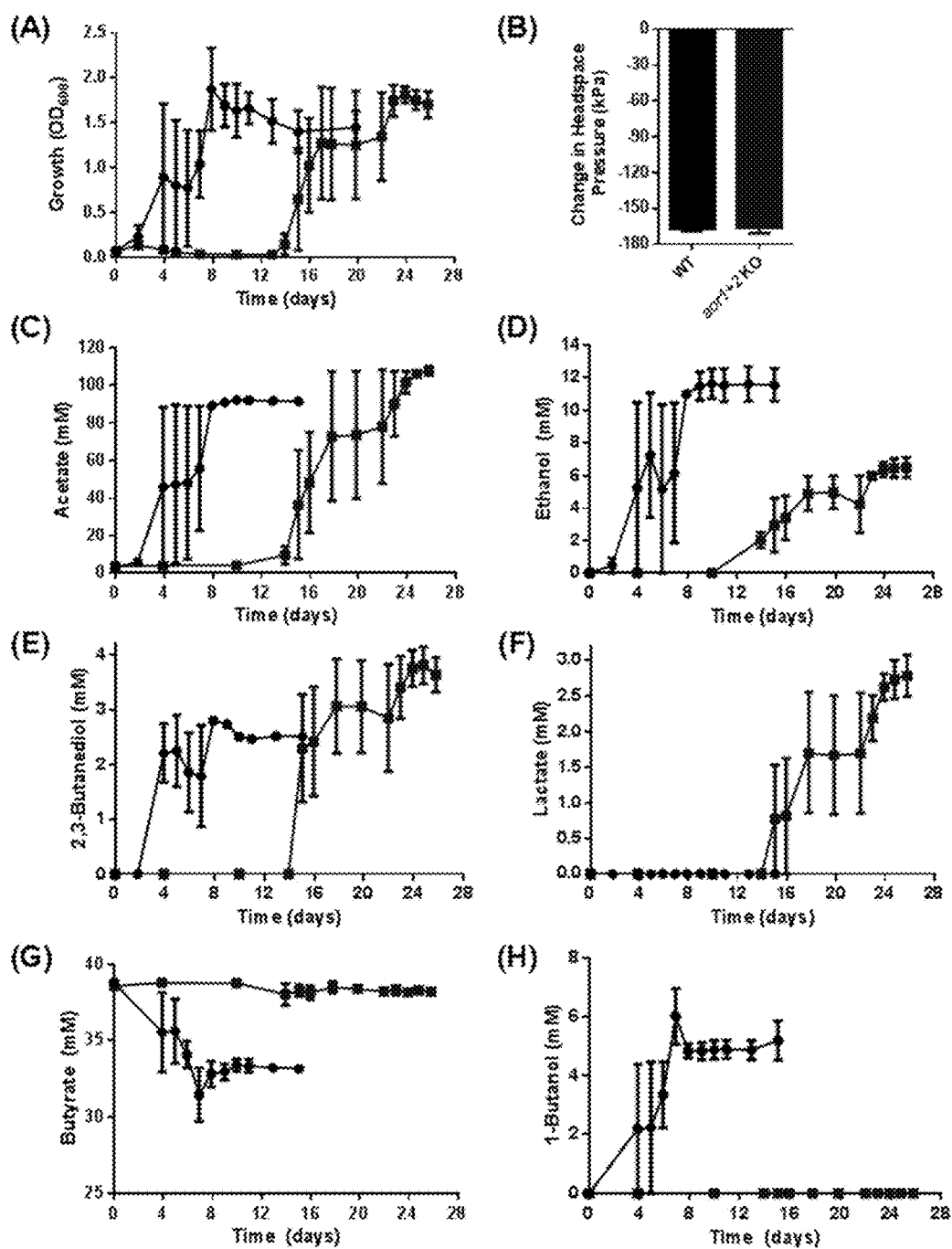

FIG. 13 is a set of graphs showing growth, headspace pressure and metabolite profiles of *C. autoethanogenum* WT and aor1+2 KO strain in the presence of 40 mM butyrate and 200 kPa CO. (A) Growth profile; (B) Change in headspace pressure; (C) Acetate profile; (D) Ethanol profile; (E) 2,3-Butanediol profile; (F) Lactate profile; (G) Propionate profile; and (H) 1-Propanol profile. Circles=WT; Squares=aor1+2 KO strain; n=3; Error bars=s.e.m.

Figure 14:
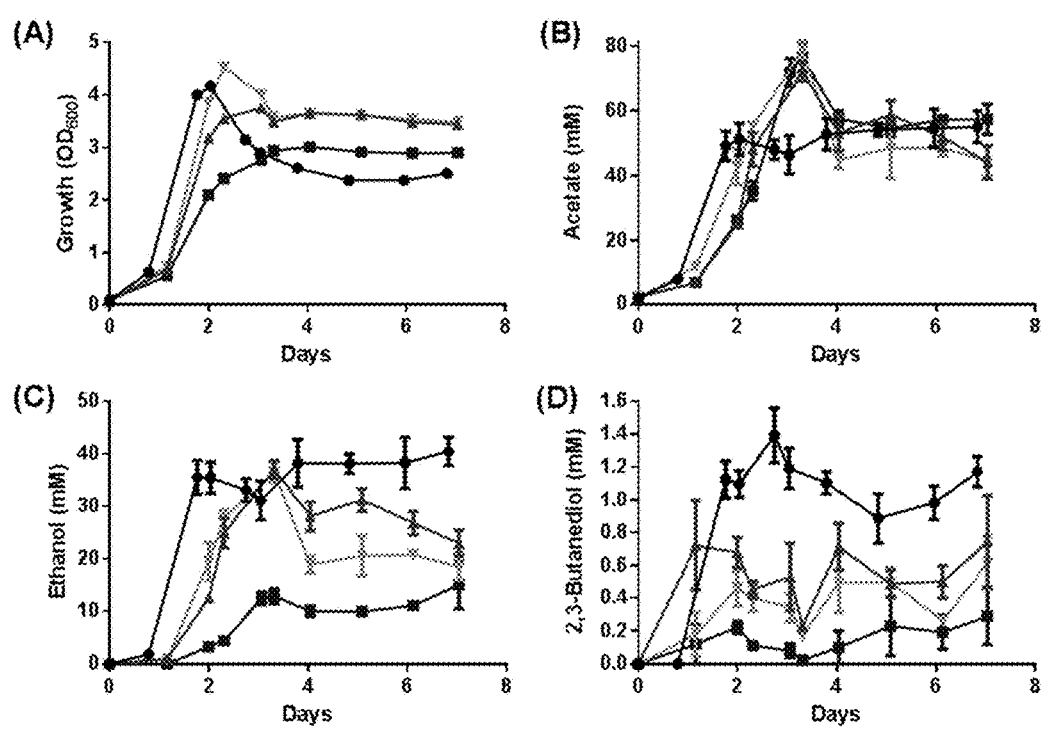

FIG. 14 is a set of graphs showing growth and metabolite profiles of *C. autoethanogenum* WT and adhE KO strains on fructose. (A) Growth profile; (B) Acetate profile; (C) Ethanol profile; and (D) 2,3-Butanediol profile. Circles=WT (n=4); Triangles=adhE1a KO strain (n=3); Inverted triangles=adhE1b KO strain (n=3); Squares=adhE2 KO strain (n=3); Error bars=s.e.m.

Figure 15:
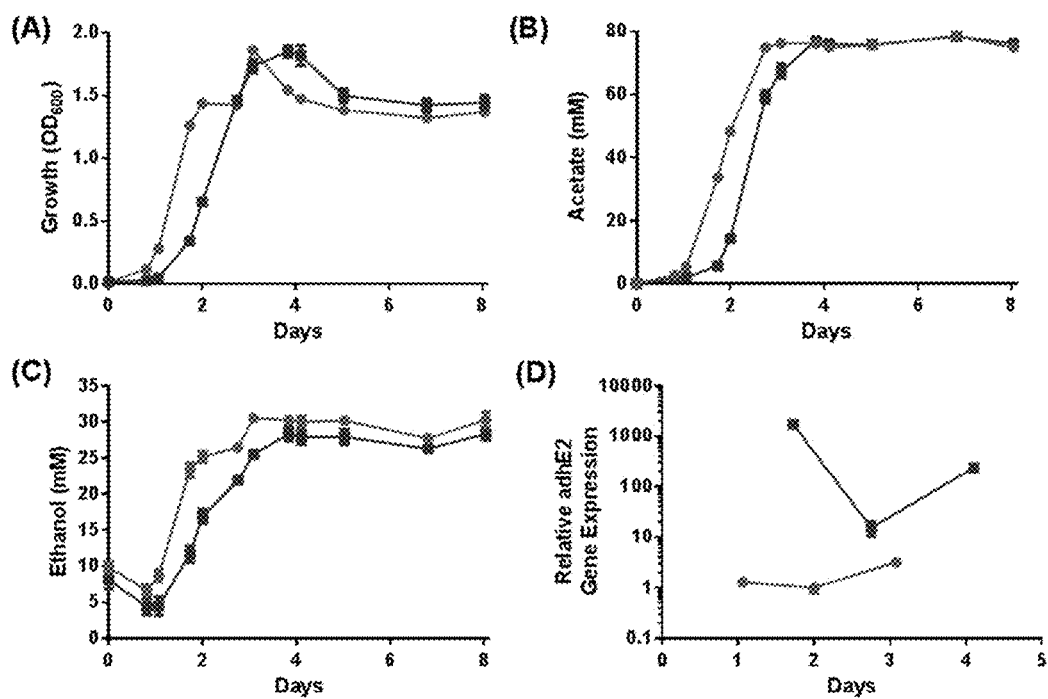

FIG. 15 is a set of graphs showing growth, metabolite and adhE2 transcript profiles of *C. autoethanogenum* ΔpyrE and ΔadhE1mut strains on fructose. (A) Growth profile; (B) Acetate profile; (C) Ethanol profile; and (D) Relative adhE2 mRNA profile. Circles=ΔpyrE (n=3); Squares=ΔadhE1mut (n=3). Error bars=s.e.m.

Figure 16:
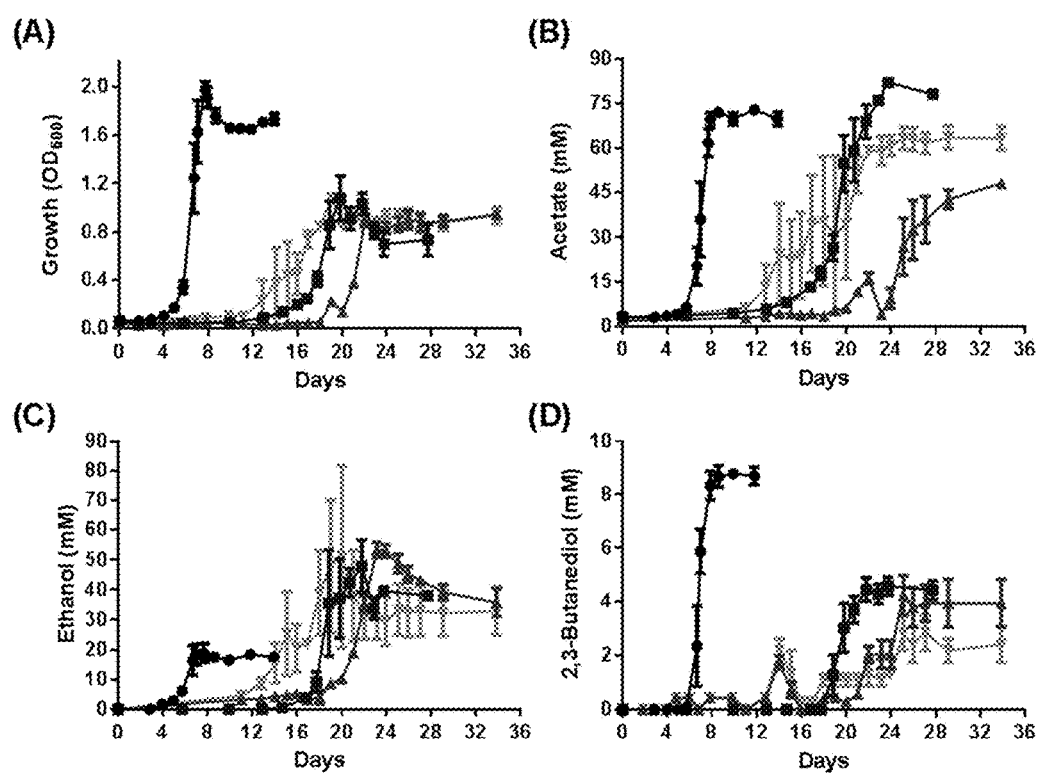

FIG. 16 is a set of graphs showing growth and metabolite profiles of *C. autoethanogenum* WT and adhE KO strains on CO. (A) Growth profile; (B) Acetate profile; (C) Ethanol profile; and (D) 2,3-Butanediol profile. Circles=WT (n=4); Triangles=adhE1a KO strain (n=3); Inverted triangles=adhE1b KO strain (n=2); Squares=adhE2 KO strain (n=3); Error bars=s.e.m.

Figure 17:
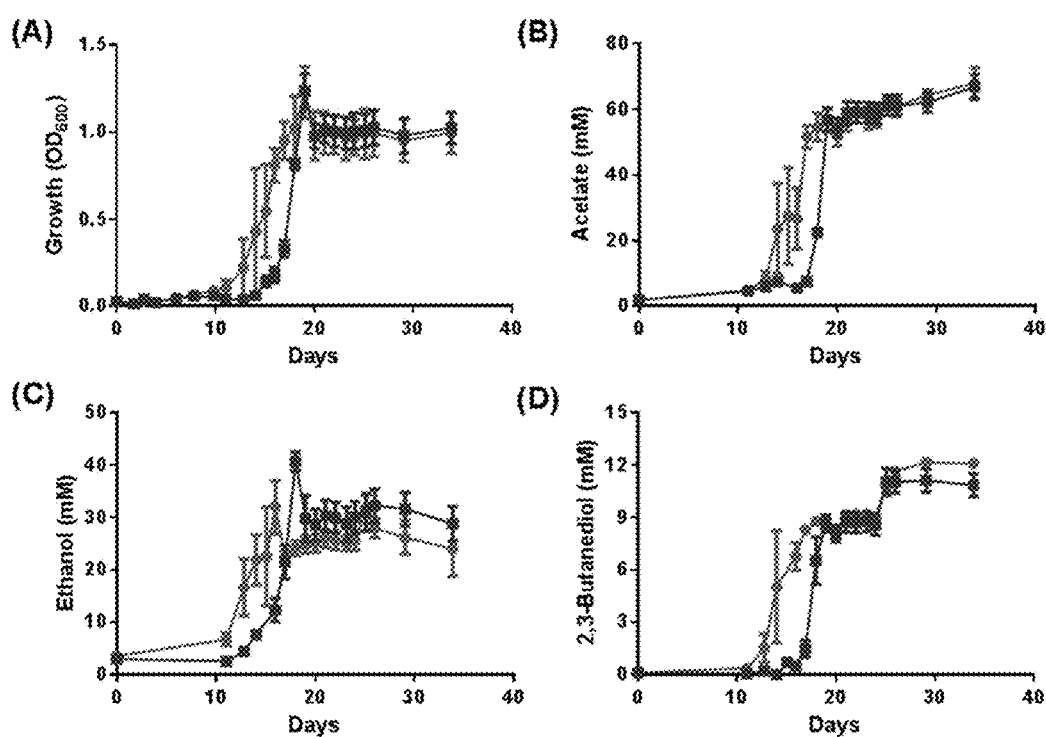

FIG. 17 is a set of graphs showing growth and metabolite profiles of *C. autoethanogenum* ΔpyrE and ΔadhE1mut strains on 200 kPa CO. (A) Growth profile; (B) Acetate profile; (C) Ethanol profile; and (D) 2,3-butanediol profile. Circles=ΔpyrE (n=3); Squares=ΔadhE1mut (n=3). Error bars=s.e.m.

DETAILED DESCRIPTION OF THE INVENTION

Many microorganisms rely on the enzymatic conversion of acids to aldehydes to support core metabolic functions. Aldehyde:ferredoxin oxidoreductase (AOR) (EC 1.2.7.5) performs this function in a number of archaea and bacteria, catalyzing the reaction of an acid, such as acetic acid (acetate), and reduced ferredoxin to form an aldehyde, such as acetaldehyde, and oxidized ferredoxin.

Figure 1:
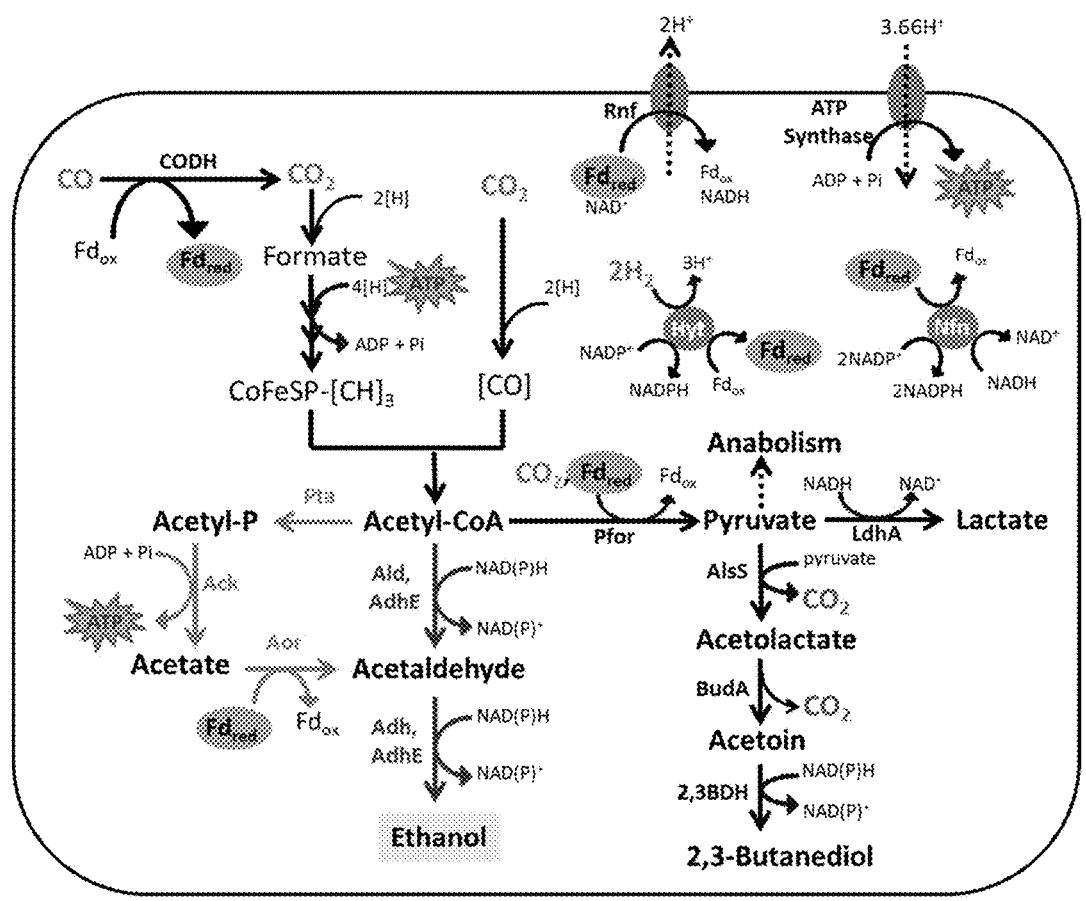
FIG. 1 is a diagram of the acetogenic ethanol biosynthesis pathway in *C. autoethanogenum*. The ATP-efficient, indirect ethanol route employing phosphotransacetylase (Pta), acetate kinase (Ack) and aldehyde:ferredoxin oxidoreductase (AOR) are shown at the far left. The direct ethanol biosynthesis route utilizing bi-functional aldehyde/alcohol dehydrogenase (AdhE) or CoA-dependent acetaldehyde dehydrogenase (Ald) and alcohol dehydrogenase (Adh) is shown in the middle. AlsS=acetolactate synthase; 2,3-BDH=2,3-butanediol dehydrogenase; BudA=acetolactate decarboxylase; CODH=carbon monoxide dehydrogenase; CoFeSP=corrinoid iron sulphur protein; Fdox=oxidized ferredoxin; Fdred=reduced ferredoxin; HytABCDE=NADP-dependent electron bifurcating hydrogenase; Nfn=transhydrogenase; Pfor=pyruvate:ferredoxin oxidoreductase; Rnf=$H^+$-translocating ferredoxin: $NAD^+$-oxidoreductase.

AOR is especially critical in ethanol-producing Wood-Ljungdahl microorganisms. The Wood-Ljungdahl pathway, also known as the reductive acetyl-CoA pathway, is the only linear $CO_2$ fixation pathway to acetyl-CoA (Drake, *Ann NY Acad Sci*, 1125: 100-128, 2008) and is considered to be the most efficient non-photosynthetic carbon fixation mechanism (Fast, *Curr Opin Chem Eng*, 1: 380-395, 2012). Briefly, the Wood-Ljungdahl pathway consists of two branches, a methyl (Eastern) and a carbonyl (Western) branch (FIG. 1). In the methyl branch, $CO_2$ is reduced to formate. Next, the formate is activated by condensation with tetrahydrofolate (THF) to form formyl-THF, consuming one molecule of ATP. Over several reactions, formyl-THF is reduced to methyl-THF. In the final step of the methyl branch, the methyl group is transferred to a corrinoid iron-sulfur-containing protein (CoFeSP) and then fused to a molecule of CO from the carbonyl branch to form acetyl-CoA via the bifunctional carbon monoxide dehydrogenase/acetyl-CoA synthase (CODH/ACS) complex. When grown autotrophically on CO, the $CO_2$ required for the methyl branch is generated by the CODH-catalyzed water-gas shift reaction. Likewise, during autotrophic growth on $CO_2$, the CO is formed from $CO_2$ by CODH in the carbonyl branch.

In particular, the ethanol biosynthesis pathway of acetogenic ethanol producers comprises two main routes (FIG. 1): (i) the direct, two-step sequential reduction of acetyl-CoA into ethanol via acetaldehyde using bi-functional aldehyde/alcohol dehydrogenase (AdhE) or aldehyde dehydrogenase (Ald) and alcohol dehydrogenase (Adh) as found in other ethanol producing bacteria including *E. coli* (Membrillo-Hernandez, *J Bacteriol*, 181: 7571-7579, 1999), and; (ii) an indirect route that proceeds via acetate and employs aldehyde:ferredoxin oxidoreductase (AOR) to first reduce acetate to acetaldehyde before ethanol synthesis via Adh (Köpke, *PNAS USA*, 107: 13087-13092, 2010; Mock, *J Bacteriol*, 197: 2965-2980, 2015).

One key distinction between the two ethanol biosynthesis routes is that the indirect route reduces acetate, which is generally considered an unwanted byproduct in industrial fermentations, since it limits the yield of products and is known to be toxic at elevated concentrations. All naturally isolated acetogens form acetate as it provides an advantage through conservation of one ATP per mole of acetate via substrate level phosphorylation (SLP), which is significant under the ATP-limiting conditions of autotrophic growth. Thermodynamic and stoichiometric analyses estimated that during acetogenic growth of *C. autoethanogenum* on $H_2+CO_2$, the ATP yield is only 0.5 ATP/mol ethanol via acetyl-CoA reduction to acetaldehyde, in comparison to the 1.2 ATP/mol ethanol via acetate reduction to ethanol (Mock, *J Bacteriol*, 197: 2965-2980, 2015).

Accordingly, indirect ethanol production via AOR confers benefits relating to both energy conservation and acetate reduction compared to direct ethanol production via aldehyde dehydrogenase and alcohol dehydrogenase. As this enzyme plays such a key role in metabolism, disruption of AOR has never previously been demonstrated in any bacterial species. Surprisingly, however, the inventors have discovered that genetically modifying a bacterium to reduce or eliminate AOR activity renders the bacterium more suitable for the production of certain types of products.

In particular, reduction or elimination of AOR activity reduces carbon flux to ethanol and increases carbon flux to other non-ethanol products. For example, the microorganism of the invention may be used to produce one or more products selected from the group consisting of acetyl-CoA, acetoacetyl-CoA, acetoacetate, acetone, isopropanol, 3-hydroxyisovaleryl-CoA, 3-hydroxyisovalerate, isobutylene, isoprene, 3-hydroxybutyryl-CoA, 3-hydroxybutyrate, 3 hydroxybutyrylaldehyde, 1,3-butanediol, 2-hydroxyisobutyryl-CoA, 2 hydroxyisobutyrate, pyruvate, acetolactate, acetoin, 2,3-butanediol and lactate.

Definitions and Background

The term "non-naturally occurring" when used in reference to a microorganism is intended to mean that the microorganism has been modified by the hand of man and has at least one genetic modification not found in a naturally occurring strain of the referenced species, i.e., not found in the wild-type strain of the referenced species.

The terms "genetic modification," "genetic alteration," or "genetic engineering" broadly refer to manipulation of the genome or nucleic acids of a microorganism. Likewise, the term "genetically engineered" refers to a microorganism comprising a manipulated genome or nucleic acids. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms. As used herein, the term "recombinant" may also be used to describe a microorganism that comprises a mutated nucleic acid or protein, including a mutated form of an endogenous nucleic acid or protein.

"Wild type" refers to the typical form of an organism, strain, gene, or characteristic as it occurs in nature, as distinguished from mutant or variant forms.

"Endogenous" refers to a nucleic acid or protein that is present or expressed in the wild-type or parental microorganism from which the microorganism of the invention is derived. For example, an endogenous gene is a gene that is natively present in the wild-type or parental microorganism from which the microorganism of the invention is derived. In one embodiment, the expression of an endogenous gene may be controlled by an exogenous regulatory element, such as an exogenous promoter.

"Exogenous" refers to a nucleic acid or protein that is not present in the wild-type or parental microorganism from which the microorganism of the invention is derived. In one embodiment, an exogenous gene or enzyme may be derived from a heterologous (i.e., different) strain or species and introduced to or expressed in the microorganism of the invention. In another embodiment, an exogenous gene or enzyme may be artificially or recombinantly created and introduced to or expressed in the microorganism of the invention. Exogenous nucleic acids may be adapted to integrate into the genome of the microorganism of the invention or to remain in an extra-chromosomal state in the microorganism of the invention, for example, in a plasmid.

The terms "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides or nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene products."

The terms "polypeptide", "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics.

"Enzyme activity," or simply "activity," refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

"Mutated" refers to a nucleic acid or protein that has been modified in the microorganism of the invention compared to the wild-type or parental microorganism from which the microorganism of the invention is derived. In one embodiment, the mutation may be a deletion, insertion, or substitution in a gene encoding an enzyme. In another embodiment, the mutation may be a deletion, insertion, or substitution of one or more amino acids in an enzyme.

In particular, a "disruptive mutation" is a mutation that reduces or eliminates (i.e., "disrupts") the expression or activity of a gene or enzyme. The disruptive mutation may partially inactivate, fully inactivate, or delete the gene or enzyme. The disruptive mutation may be a knockout (KO) mutation. The disruptive mutation may be any mutation that reduces, prevents, or blocks the biosynthesis of a product produced by an enzyme. In microorganisms with multiple isoforms of an enzyme, one or more disruptive mutations may be introduced to reduce or eliminate expression or activity of a single isoform, of two or more isoforms, or of all isoforms of the enzyme. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The disruptive mutation may be introduced using any method known in the art.

Introduction of a disruptive mutation results in a microorganism of the invention that produces no acetaldehyde and/or ethanol or substantially no acetaldehyde and/or ethanol or a reduced amount of acetaldehyde and/or ethanol compared to the parental microorganism from which the microorganism of the invention is derived. For example, the microorganism of the invention may produce no acetaldehyde and/or ethanol or at least about 1%, 3%, 5%, 10%, 20%, 30%, 40%, 50%, 60%, 70%, 80%, 90%, or 95% less acetaldehyde and/or ethanol than the parental microorganism. For example, the microorganism of the invention may produce less than about 0.001, 0.01, 0.10, 0.30, 0.50, or 1.0 g/L acetaldehyde and/or ethanol.

The term "variants" includes nucleic acids and proteins whose sequence varies from the sequence of a reference nucleic acid and protein, such as a sequence of a reference nucleic acid and protein disclosed in the prior art or exemplified herein. The invention may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

A "microorganism" is a microscopic organism, especially a bacterium, archea, virus, or fungus. The microorganism of the invention is typically a bacterium. As used herein, recitation of "microorganism" should be taken to encompass "bacterium."

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism.

The microorganism of the invention may be further classified based on functional and/or structural characteristics. For example, the microorganism of the invention may be or may be derived from a C1-fixing microorganism, an anaerobe, an acetogen, an ethanologen, a carboxydotroph, and/or a methanotroph. Table 1 provides a representative list of microorganisms, identifying some of their functional and structural characteristics.

TABLE 1

|  | C1-fixing | Anaerobe | Acetogen | Ethanologen | Autotroph | Carboxydotroph | Methanotroph | AOR (EC 1.2.7.5) | AdhE (EC 1.2.1.10/ EC 1.1.1.1) |
|---|---|---|---|---|---|---|---|---|---|
| *Acetobacterium woodii* | + | + | + | +/−[1] | − | − | − | − | + |
| *Alkalibaculum bacchii* | + | + | + | + | + | + | − | + | +/−[7] |
| *Blautia producta* | + | + | + | − | + | + | − | +/−[7] | +/−[7] |
| *Butyribacterium methylotrophicum* | + | + | + | + | + | + | − | +/−[7] | +/−[7] |
| *Clostridium aceticum* | + | + | + | − | + | + | − | + | − |
| *Clostridium autoethanogenum* | + | + | + | + | + | + | − | + | + |
| *Clostridium carboxidivorans* | + | + | + | + | + | + | − | + | + |

TABLE 1-continued

| | C1-fixing | Anaerobe | Acetogen | Ethanologen | Autotroph | Carboxydotroph | Methanotroph | AOR (EC 1.2.7.5) | AdhE (EC 1.2.1.10/ EC 1.1.1.1) |
|---|---|---|---|---|---|---|---|---|---|
| *Clostridium coskatii* | + | + | + | + | + | + | − | + | + |
| *Clostridium drakei* | + | + | + | − | + | + | − | +/−[7] | +/−[7] |
| *Clostridium formicoaceticum* | + | + | + | − | + | + | − | + | +/−[7] |
| *Clostridium ljungdahlii* | + | + | + | + | + | + | − | + | + |
| *Clostridium magnum* | + | + | + | − | + | +/−[2] | − | − | + |
| *Clostridium ragsdalei* | + | + | + | + | + | + | − | + | + |
| *Clostridium scatologenes* | + | + | + | − | + | + | − | − | + |
| *Eubacterium limosum* | + | + | + | − | + | + | − | + | − |
| *Moorella thermautotrophica* | + | + | + | + | + | + | − | +/−[7] | +/−[7] |
| *Moorella thermoacetica* (formerly *Clostridium thermoaceticum*) | + | + | + | −[3] | + | + | − | + | − |
| *Oxobacter pfennigii* | + | + | + | − | + | + | − | − | − |
| *Sporomusa ovata* | + | + | + | − | + | +/−[4] | − | + | − |
| *Sporomusa silvacetica* | + | + | + | − | + | +/−[5] | − | +/−[7] | +/−[7] |
| *Sporomusa sphaeroides* | + | + | + | − | + | +/−[6] | − | +/−[7] | +/−[7] |
| *Thermoanaerobacter kiuvi* | + | + | + | − | + | − | − | − | − |

[1]*Acetobacterium woodi* can produce ethanol from fructose, but not from gas.
[2]It has not been investigated whether *Clostridium magnum* can grow on CO.
[3]One strain of *Moorella thermoacetica*, *Moorella* sp. HUC22-1, has been reported to produce ethanol from gas.
[4]It has not been investigated whether *Sporomusa ovata* can grow on CO.
[5]It has not been investigated whether *Sporomusa silvacetica* can grow on CO.
[6]It has not been investigated whether *Sporomusa sphaeroides* can grow on CO.
[7]It is currently unknown whether this enzyme is present in this species.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1.

An "anaerobe" is a microorganism that does not require oxygen for growth. An anaerobe may react negatively or even die if oxygen is present above a certain threshold. Typically, the microorganism of the invention is an anaerobe. In a preferred embodiment, the microorganism of the invention is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). Acetogens use the acetyl-CoA pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. Typically, the microorganism of the invention is an acetogen. In a preferred embodiment, the microorganism of the invention is derived from an acetogen identified in Table 1.

An "ethanologen" is a microorganism that produces or is capable of producing ethanol. In certain embodiments, the microorganism of the invention is an ethanologen. In a preferred embodiment, the microorganism of the invention is derived from an ethanologen identified in Table 1. However, since AOR and AdhE are involved in ethanol biosynthesis, disruption of the AOR and/or AdhE of a microorganism may result in altered phenotype with respect to ethanol production.

An "autotroph" is a microorganism capable of growing in the absence of organic carbon. Instead, autotrophs use inorganic carbon sources, such as CO and/or $CO_2$. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon. Typically, the microorganism of the invention is a carboxydotroph. In a preferred embodiment, the microorganism of the invention is derived from a carboxydotroph identified in Table 1.

A "methanotroph" is a microorganism capable of utilizing methane as a sole source of carbon and energy. In certain embodiments, the microorganism of the invention is a methanotroph or is derived from a methanotroph. In other embodiments, the microorganism of the invention is not a methanotroph or is not derived from a methanotroph.

The parental microorganism from which the microorganism of the invention is derived generally comprises an enzyme that catalyzes the reaction defined by EC 1.2.7.5. This enzyme is responsible for the conversion of acids into their corresponding aldehydes. More specifically, this enzyme catalyzes the conversion of a carboxylate+$2H^+$+2 reduced ferredoxin to an aldehyde+$H_2O$+2 oxidized ferredoxin. In a preferred embodiment, the enzyme that catalyzes this reaction is AOR.

In acetogens, the activity of AOR can be coupled to oxidation CO (via CO dehydrogenase, EC 1.2.7.4) or hydrogen (via ferredoxin-dependent hydrogenase, EC 1.12.7.2 or 1.12.1.4) that both yield reduced ferredoxin (Köpke, Curr Opin Biotechnol 22: 320-325, 2011; Köpke, PNAS USA, 107: 13087-13092, 2010). For instance, the genome of C. autoethanogenum encodes two aor isoforms (CAETHG_0092 and 0102) and two adhE genes (CAETHG_3747 and 3748) that appear in tandem and are potentially a result of gene duplication (Brown, Biotechnol Biofuels, 7: 1-18, 2014). The same arrangement is also found in C. ljungdahlii (Köpke, PNAS USA, 107: 13087-13092, 2010; Leang, Appl Environ Microbiol, 79: 1102-1109, 2013).

Preferably, the parental microorganism is a bacterium selected from the group consisting of Alkalibaculum bacchi, Blautia product, Butyribacterium methylotrophicum, Chloroflexus aurantiacus, Clostridium aceticum, Clostridium acetobutylicum, Clostridium autoethanogenum, Clostridium botulinum, Clostridium carboxidivorans, Clostridium coskatii, Clostridium drakei, Clostridium formicoaceticum, Clostridium ljungdahlii, Clostridium ragsdalei, Desulfovibrio vulgaris, Eubacterium limosum, Geobacter sulfurreducens, Methylomicrobium alcaliphilum, Moorella thermoautrophica, Moorella thermoacetica, Rhodospirillum rubrum, Sporomusa ovata, Sporomusa silvacetica, Sporomusa sphaeroides, Thermanaerovibrio acidaminovorans, Thermanaerovibrio acidaminovorans, Thermoanaerobacter wiegelii, Thermodesulfovibrio yellowstonii, Thermodesulfovibrio yellowstonii, and Thermus thermophilus. In one embodiment, the parental microorganism is Clostridium autoethanogenum, Clostridium ljungdahlii, Clostridium ragsdalei, or Clostridium coskatii. In a preferred embodiment, the parental microorganism is Clostridium autoethanogenum LZ1561, which was deposited on Jun. 7, 2010 with Deutsche Sammlung von Mikroorganismen and Zellkulturen GmbH (DSMZ) located at Inhoffenstraβ 7B, D-38124 Braunschweig, Germany on Jun. 7, 2010 under the terms of the Budapest Treaty and accorded accession number DSM23693.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism selected from the group consisting of Alkalibaculum bacchi, Blautia product, Butyribacterium methylotrophicum, Chloroflexus aurantiacus, Clostridium aceticum, Clostridium acetobutylicum, Clostridium autoethanogenum, Clostridium botulinum, Clostridium carboxidivorans, Clostridium coskatii, Clostridium drakei, Clostridium formicoaceticum, Clostridium ljungdahlii, Clostridium ragsdalei, Desulfovibrio vulgaris, Eubacterium limosum, Geobacter sulfurreducens, Methylomicrobium alcaliphilum, Moorella thermoautrophica, Moorella thermoacetica, Rhodospirillum rubrum, Sporomusa ovata, Sporomusa silvacetica, Sporomusa sphaeroides, Thermanaerovibrio acidaminovorans, Thermanaerovibrio acidaminovorans, Thermoanaerobacter wiegelii, Thermodesulfovibrio yellowstonii, Thermodesulfovibrio yellowstonii, and Thermus thermophilus. In one embodiment, the microorganism of the invention is derived from Clostridium autoethanogenum, Clostridium ljungdahlii, Clostridium ragsdalei, or Clostridium coskatii. In a preferred embodiment, the microorganism of the invention is derived from Clostridium autoethanogenum LZ1561, which is deposited under DSMZ accession number DSM23693.

The following table provides an exemplary list of microorganisms comprising AOR genes/enzymes.

| Enzyme | Microorganism | Accession | GeneID |
|---|---|---|---|
| AOR | Alkalibaculum bacchi | | |
| AOR | Blautia producta | NZ_ARET00000000.1 | |
| AOR | Butyribacterium methylotrophicum | | |
| AOR | Chloroflexus aurantiacus J-10-fl | NC_010175.1 | 5828639 |
| AOR | Clostridium aceticum | | |
| AOR | Clostridium acetobutylicum ATCC 824 | NC_003030.1 | 1118201 |
| AOR | Clostridium autoethanogenum | NC_022592.1 | CAETHG_0092 |
| AOR | Clostridium autoethanogenum | NC_022592.1 | CAETHG_0102 |
| AOR | Clostridium botulinum A str. Hall | NC_009698.1 | 5400593 |
| AOR | Clostridium carboxidivorans | | |
| AOR | Clostridium coskatii | | |
| AOR | Clostridium drakei | | |
| AOR | Clostridium formicoaceticum | | |
| AOR | Clostridium ljungdahlii | NC_014328.1 | CLJU_c20110 |
| AOR | Clostridium ljungdahlii | NC_14328.1 | CLJU_c20210 |
| AOR | Clostridium ragsdalei | | |
| AOR | Desulfovibrio vulgaris str. Hildenborough | NC_002937.3 | 2796664 |
| AOR | Desulfovibrio vulgaris str. Hildenborough | NC_002937.3 | 2795337 |
| AOR | Eubacterium limosum | NC_014624.2 | ELI_1752 |
| AOR | Geobacter sulfurreducens PCA | NC_002939.5 | 2685730 |
| AOR | Geobacter sulfurreducens PCA | NC_002939.5 | 2687039 |
| AOR | Methylomicrobium alcaliphilum 20Z | NC_016112.1 | 11361147 |
| AOR | Moorella thermoautrophica | CP012369.1 | Moth_0154 |
| AOR | Moorella thermoautrophica | CP012369.1 | Moth_2300 |
| AOR | Moorella thermoautrophica | CP012369.1 | Moth_0722 |
| AOR | Moorella thermoacetica ATCC 39073 | NC_007644.1 | 3831332 |
| AOR | Moorella thermoacetica ATCC 39073 | NC_007644.1 | 3830998 |
| AOR | Moorella thermoacetica ATCC 39073 | NC_007644.1 | 3831866 |
| AOR | Rhodospirillum rubrum ATCC 11170 | NC_007643.1 | 3833668 |
| AOR | Sporomusa ovata | | |
| AOR | Sporomusa silvacetica | | |
| AOR | Sporomusa sphaeroides | | |

| Enzyme | Microorganism | Accession | GeneID |
|---|---|---|---|
| AOR | *Thermanaerovibrio acidaminovorans* DSM 6589 | NC_013522.1 | 8630284 |
| AOR | *Thermanaerovibrio acidaminovorans* DSM 6589 | NC_013522.1 | 8630027 |
| AOR | *Thermanaerovibrio acidaminovorans* DSM 6589 | NC_013522.1 | 8630623 |
| AOR | *Thermoanaerobacter wiegelii* Rt8.B1 | NC_15958.1 | 11082596 |
| AOR | *Thermodesulfovibrio yellowstonii* | NC_11296.1 | 6941429 |
| AOR | *Thermodesulfovibrio yellowstonii* | NC_11296.1 | 6943174 |
| AOR | *Thermodesulfovibrio yellowstonii* | NC_11296.1 | 6941905 |
| AOR | *Thermus thermophilus* HB8 | NC_006461.1 | 3168554 |
| AOR | *Thermus thermophilus* HB8 | NC_006461.1 | 3168612 |

In a preferred embodiment, the microorganism of the invention is derived from the cluster of Clostridia comprising the species *Clostridium autoethanogenum, Clostridium ljungdahlii, Clostridium ragsdalei,* and *Clostridium coskatii*. These species were first reported and characterized by Abrini, *Arch Microbiol,* 161: 345-351, 1994 (*Clostridium autoethanogenum*), Tanner, *Int J System Bacteriol,* 43: 232-236, 1993 (*Clostridium ljungdahlii*), and Huhnke, WO 2008/028055 (*Clostridium ragsdalei*).

These species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 µm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng,* 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol,* 22: 320-325, 2011).

Thus, in summary, many of the characteristics of *Clostridium autoethanogenum, Clostridium ljungdahlii, Clostridium ragsdalei,* or *Clostridium coskatii* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum, Clostridium ljungdahlii, Clostridium ragsdalei,* or *Clostridium coskatii*. Isolates and mutants of *Clostridium autoethanogenum* include JA1-1 (DSM10061) (Abrini, *Arch Microbiol,* 161: 345-351, 1994), LBS1560 (DSM19630) (WO 2009/064200), and LZ1561 (DSM23693). Isolates and mutants of *Clostridium ljungdahlii* include ATCC 49587 (Tanner, *Int J Syst Bacteriol,* 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), 0-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

Additionally or alternatively, the parental microorganism from which the microorganism of the invention is derived may comprise an enzyme that catalyzes the reaction defined by EC 1.2.1.10/EC 1.1.1.1, e.g., AdhE. The microorganism of the invention may have decreased or eliminated activity of at least one enzyme that catalyzes the reaction defined by EC 1.2.1.10 and/or EC 1.1.1.1 compared to the parental bacterium, such as at least one disruptive mutation in a gene encoding the enzyme that catalyzes the reaction defined by EC 1.2.1.10 and/or EC 1.1.1.1. The enzyme that catalyzes the reaction defined by EC 1.2.1.10 and/or EC 1.1.1.1 is preferably selected from the group consisting of bifunctional aldehyde/alcohol dehydrogenase, aldehyde dehydrogenase, and alcohol dehydrogenase. Disrupting the expression of one or more of these enzymes may further direct carbon flux away from ethanol and towards non-ethanol products.

"Substrate" refers to a carbon and/or energy source for the microorganism of the invention. Typically, the substrate is gaseous and comprises a C1-carbon source, for example, $CO$, $CO_2$, and/or $CH_4$. Preferably, the substrate comprises a C1-carbon source of CO or CO+$CO_2$. The substrate may further comprise other non-carbon components, such as $H_2$, $N_2$, or electrons. In certain embodiments, the substrate may also comprise carbohydrates, such as glucose or lignocellulose.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The microorganism of the invention may be cultured to produce one or more products. For instance, Clostridium autoethanogenum produces or can be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene and other terpenes (WO 2013/180584), mevalonic acid (WO 2013/180584), fatty acids (WO 2013/191567), 2-butanol (WO 2013/185123), 1,2-propanediol (WO 2014/0369152), and 1-propanol (WO 2014/0369152), para-hydroxybenzoic acid (WO 2016/191625), salicylate (WO 2016/191625), 2-aminobenzoate (WO 2016/191625), dihydroxybenzoate (WO 2016/191625), 4-hydroxycyclohexane carboxylic acid (WO 2016/191625), 3-hydroxybutyrate (WO 2017/066498), 1,3-butanediol (WO 2017/066498), 2-hydroxyisobutyrate (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), or isoamyl alcohol (WO 2017/066498). In addition to one or more of these products, the microorganism of the invention may also produce ethanol, acetate, and/or 2,3-butanediol. In certain embodiments, microbial biomass itself may be considered a product.

A "native product" is a product produced by a genetically unmodified microorganism. For example, ethanol, acetate, and 2,3-butanediol are native products of Clostridium autoethanogenum, Clostridium ljungdahlii, Clostridium ragsdalei, and Clostridium coskatii. A "non-native product" is a product that is produced by a genetically modified microorganism, but is not produced by a genetically unmodified (e.g., parental) microorganism from which the genetically modified microorganism is derived. Pathways and enzymes for producing non-native products can be found in the art, such as those referenced above.

"Selectivity" refers to the ratio of the production of a desired product to the production of all fermentation products produced by a microorganism. The microorganism of the invention may be engineered to produce products at a certain selectivity or at a minimum selectivity. In one embodiment, a desired product account for at least about 5%, 10%, 15%, 20%, 30%, 50%, or 75% of all fermentation products produced by the microorganism of the invention. In one embodiment, the desired product accounts for at least 10% of all fermentation products produced by the microorganism of the invention, such that the microorganism of the invention has a selectivity for the desired product of at least 10%. In another embodiment, the desired product accounts for at least 30% of all fermentation products produced by the microorganism of the invention, such that the microorganism of the invention has a selectivity for the desired product of at least 30%.

"Increasing the efficiency," "increased efficiency," and the like include, but are not limited to, increasing growth rate, product production rate or volume, product volume per volume of substrate consumed, or product selectivity. Efficiency may be measured relative to the performance of parental microorganism from which the microorganism of the invention is derived.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the desired product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

In certain embodiments, the fermentation is performed in the absence of light or in the presence of an amount of light insufficient to meet the energetic requirements of photosynthetic microorganisms.

Products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, products are recovered from the fermentation broth by continuously removing a portion of the broth from the bioreactor, separating microbial cells from the broth (conveniently by filtration), and recovering one or more products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after products have been removed is also preferably returned to the bioreactor. Additional nutrients (such as B vitamins) may be added to the cell-free permeate to replenish the medium before it is returned to the bioreactor.

EXAMPLES

The following examples further illustrate the invention but, of course, should not be construed to limit its scope in any way.

Example 1

This example demonstrates the successful introduction of disruptive mutations in AOR and alcohol dehydrogenase in *C. autoethanogenum*.

1.1 Bacterial Strains and Growth Conditions

The bacterial strains used in this example are described in Table 2.

TABLE 2

| Strain | Description/Genotype |
|---|---|
| *Escherichia coli* CA434 (HB101) | Conjugative transfer strain. Strain HB101 [thi-I hsdS20 ($r_5$, $m_5$) supE44 recAB ara-14 leuB5proA2 lacYl galKl rpsL20 ($Str^R$)xyl-5 mt1-1] carrying the Tra$^+$, Mob$^+$ plasmid R702 [R702-Tc$^R$, Sm$^R$, Su$^R$, Hg$^R$] |
| *Clostridium autoethanogenum* DSM 10061 | Wild-type isolate |
| *C. autoethanogenum* CauDSM10061-adhE1a-115s::CT | Group II intron directionally inserted at upstream Ald domain of adhE1 (CAETHG_3747) gene locus |
| *C. autoethanogenum* CauDSM10061-adhE1b-541s::CT | Group II intron directionally inserted at downstream Adh domain of adhE1 (CAETHG_3747) gene locus |
| *C. autoethanogenum* CauDSM10061-adhE2-662s::CT | Group II intron directionally inserted at adhE2 (CAETHG_3748) gene locus |
| *C. autoethanogenum* CauDSM10061-aor1-361s::CT | Group II intron directionally inserted at aor1 (CAETHG_0092) gene locus |
| *C. autoethanogenum* CauDSM10061-aor2-370s::CT | Group II intron directionally inserted at aor2 (CAETHG_0102) gene locus |
| *C. autoethanogenum* ΔpyrE in-frame deletion strain | pyrE in-frame deletion created via Allele-Coupled Exchange |
| *C. autoethanogenum* ΔadhE1 in-frame deletion strain | adhE1 In-frame deletion in ΔpyrE strain |
| *C. autoethanogenum* ΔadhE1$^{mut}$ in-frame deletion strain | adhE1 In-frame deletion with unintended promoter deletion of adhE2 in ΔpyrE strain |
| *C. autoethanogenum* ΔadhE1+2 in-frame deletion strain | adhE1 and adhE2 In-frame deletion in ΔpyrE strain |
| *C. autoethanogenum* aor1+2 double KO strain | Group II intron directionally inserted at aor1 gene locus in ΔpyrE strain. Followed by aor2 in-frame deletion using pyrE-mediated allelic exchange. In final step, pyrE was restored back to WT |

*Escherichia coli* strains employed for general plasmid propagation, cloning and conjugation were cultivated at 37° C. in LB medium in the presence of antibiotic (25 µg/mL chloramphenicol, 100 µg/mL spectinomycin). *C. autoethanogenum* DSM 10061 was purchased from Deutsche Sammlung von Mikroorganismen and Zellkulturen (DSMZ) GmbH, Braunschweig, Germany and routinely cultivated under strict anaerobic conditions in CaGM medium.

Growth medium CaGM contained (per L) 0.25 g $NH_4Cl$, 0.1 g KCl, 0.2 g $KH_2PO_4$, 0.2 g $MgSO_4.7H_2O$, 0.02 g $CaCl_2.2H_2O$, 1 g yeast extract, 0.5 ml of 2 g/L resazurin, 20 g 2-(N-morpholino) ethanesulfonic acid (MES), 0.05 g $Fe(SO_4)_2.7H_2O$, 0.25 g sodium acetate.$3H_2O$, 0.05 g nitrilotriacetic acid (NTA) and 10 g of fructose (only for heterotrophic growth), 10 mL trace element solution (TSE) and 10 mL of Wolfe's vitamin solution. The TSE solution composition (per L) was: 2 g NTA, 1 g $MnSO_4.H_2O$, 0.8 g $Fe(SO_4)_2(NH_4)_2.6H_2O$, 0.2 g $CoCl_2.6H_2O$, 0.2 mg $ZnSO_4.7H_2O$, 0.02 g $CuCl_2.2H_2O$, 0.02 g $NaMoO_4.2H_2O$, 0.02 g $Na_2SeO_3$, 0.02 g $NiCl_2.6H_2O$ and 0.02 g $Na_2WO_4.2H_2O$. The vitamin solution composition (per L) was: 2 mg biotin, 2 mg folic acid, 10 mg pyridoxine hydrochloride, 5 mg thiamine HCl, 5 mg riboflavin, 5 mg nicotinic acid, 5 mg calcium pantothenate, 0.1 mg vitamin $B_{12}$, 5 mg p-aminobenzoic acid and 5 mg thioctic acid. The medium was prepared anaerobically and the pH of the medium was adjusted to 5.8 before sterilization. Prior to inoculation, 100 mL of CaGM medium was reduced with 1 mL of reducing agent 1 (4 g cysteine HCl per 100 mL water) and 1 mL of reducing agent 2 (7.64 g NTA, 5.33 g $Na_2CO_3$, and 8.5 mL $TiCl_3$ per 100 mL water).

Cell growth on liquid medium was monitored spectrophotometrically at 600 nm (OD600). Changes in headspace pressure were measured using Rugged Digital Pressure Gauge DPG120 (Omega Engineering). For growth of *C. autoethanogenum* on agar plates, YTF solid medium (10 g/L fructose, 10 g/L yeast extract, 16 g/L tryptone, 0.2 g/L sodium chloride, 15 g/L bacteriological agar (oxoid), pH 5.8), with antibiotics (7.5 µg/mL thiamphenicol, 6 µg/mL clarithromycin) where appropriate, was used. All mutagenesis work was performed inside an anaerobic workstation at 37° C. (Don Whitley Scientific Ltd). For strain comparisons, 3 to 4 biological replicates containing *C. autoethanogenum* wild-type (WT) or recombinant strains were grown in 250 mL serum bottles containing 50 mL CaGM medium with either 10 g/L fructose, 200 kPa CO, or 150 kPa H2+50 kPa $CO_2$ as growth substrate. Incubation at 37° C. was undertaken with agitation (225 rpm) inside New Brunswick Innova shakers (Eppendorf). A standardized 0.5 OD600 equivalent of exponentially growing cultures were used as inoculum.

1.2 DNA Manipulations

DNA manipulations and cloning were carried out according to standard techniques as per Sambrook (Sambrook, Molecular Cloning: A Laboratory Manual, Cold Spring Harbor Laboratory Press, New York, 2001). Genomic DNA from *C. autoethanogenum* was isolated using DNeasy Blood and Tissue kit (Qiagen) for PCR diagnostics. For Southern Blot analysis, genomic DNA of *C. autoethanogenum* was extracted according to Bertram and Dürre (Bertram, *Arch Microbiol*, 151: 551-557, 1989). Plasmid DNA from *C. autoethanogenum* was isolated using QIAprep Spin Miniprep kit (Qiagen) with the supplementation of 20 mg/mL chicken lysozyme into lysis buffer and incubation at 37° C. for 30 minute before proceeding to downstream procedures. Polymerase Chain Reaction (PCR) was carried out using Phusion DNA polymerase (NEB) or Q5 DNA polymerase (NEB). Primers used in this example are listed in Table 3. Primers were designed using Geneious (Biomatters) and synthesized by Sigma-Aldrich or Eurofins. Sanger sequencing of plasmids and amplicons was carried out by Source Bioscience Plc (Nottingham, UK).

TABLE 3

| Primer name | Function(s) |
| --- | --- |
| Univ-0027-F | Amplification and sequencing of 16s rRNA for Eubacteria; (2) |
| Univ-1492-R | |
| $P_{acsA}$-NotI-F | Amplification and cloning of acsA (CAETHG_1621) promoter region of |
| $P_{acsA}$-NdeI-R | *C. autoethanogenum* |
| aor1-NdeI-F | SOE PCR to mutate two internal NdeI restriction sites and clone aor1 |
| aor1-SOE-B1 | (CAETHG_0092) from *C. autoethanogenum* |
| aor1-SOE-C1 | |
| aor1-SOE-C2B | |
| aor1-SOE-B2B | |
| aor1-KpnI-R | |
| adhE1a-115s-F | PCR screening for integration of Intron I into upstream Ald domain of |
| adhE1a-115s-R | *C. autoethanogenum* adhE1 |
| adhE1b-541s-F | PCR screening for integration of Intron I into downstream Adh domain |
| adhE1b-541s-R | of *C. autoethanogenum* adhE1 |
| adhE2-662s-F | PCR screening for integration of Intron I into *C. autoethanogenum* |
| adhE2-662s-R | adhE2 |
| aor1-361s-F | PCR screening for integration of Intron I into *C. autoethanogenum* |
| aor1-361s-R | aor1 |
| aor2-370s-F | PCR screening for integration of Intron I into *C. autoethanogenum* |
| aor2-370s-R | aor2 |
| adhE1-IFD-F | Screening of double crossover and subsequent sequencing of *C.* |
| adhE1-IFD-R | *autoethanogenum* adhE1 |
| adhE1-seq-F | Screening of double crossover and subsequent sequencing for in- |
| adhE2-seq-R | frame deletion of *C. autoethanogenum* adhE1 and adhE2 |
| aor2-seq-F | Screening of double crossover and subsequent sequencing of *C.* |
| aor2-seq-R | *autoethanogenum* aor2 in-frame deletion |
| ACE-plasmid-F | Anneal to region prior to left homology arm (LHA) of ACE plasmid. To be used for screening of single crossover mutant at LHA |
| ACE-plasmid-R | Anneal to region prior to right homology arm (RHA) of ACE plasmid. To be used for screening of single crossover mutant at RHA |
| adhE1-ald-LHA-SacII-F | SOE-PCR to construct left homology arm for in-frame deletion of *C. autoethanogenum* adhE1 or adhE1 & 2 |

TABLE 3-continued

| Primer name | Function(s) |
|---|---|
| adhE1-IFD-LHA-R<br>adhE1-IFD-RHA-F<br>adhE1-IFD-RHA-AscI-R | SOE-PCR to construct homology arms for in-frame deletion of *C. autoethanogenum* adhE1 |
| adhE1&2-SOE-B<br>adhE1&2-SOE-C<br>adhE1&2-RHA-AscI-R | SOE-PCR to construct homology arms for in-frame deletion of *C. autoethanogenum* adhE1 & 2 |
| aor2-LHA-SacII-F<br>aor2-LHA-R<br>aor2-RHA-F<br>aor2-RHA-AscI-R | SOE-PCR to construct homology arms for in-frame deletion of *C. autoethanogenum* aor2 |

1.3 Plasmid Vectors and Allelic-Exchange Cassettes

All plasmids used in this example (Table 4) are derived from the pMTL80000 series of modular, *E. coli-Clostridium* shuttle vectors (Heap, *J Microbiol Meth,* 78: 79-85, 2009).

TABLE 4

| Plasmid | Description |
|---|---|
| pMTL83151 | *Escherichia coli/Clostridium* modular shuttle vector, pCB102, ColE1+tra, $Cm^R/Tm^R$ |
| pMTL83151-$P_{acsA}$ | Overexpression plasmid with *C. autoethanogenum* acsA (CAETHG_1621) promoter cloned between NotI and NdeI sites |
| pMTL83151-$P_{acsA}$-aor1 | Overexpression plasmid of *C. autoethanogenum* aor1 |
| pMTL84151 | *E. coli/Clostridium* modular shuttle vector, pCD6, ColE1+tra, $Cm^R/Tm^R$ |
| pMTL-AMH101 | ACE plasmid for creation of the ΔpyrE (CAETHG_1476) in-frame deletion strain in *C. autoethanogenum*. Plasmid contains functional *C. acetobutylicum* pyrE (CAC_0027) as counter selectable marker |
| pMTL-AMH102 | ACE plasmid for repair of the ΔpyrE (CAETHG_1476) in-frame deletion strain in *C. autoethanogenum* |
| pMTL84151-ΔadhE1 | ACE plasmid for the creation of adhE1 in-frame deletion in *C. autoethanogenum*. Plasmid contains a functional *C. acetobutylicum* pyrE as counter selectable marker |
| pMTL84151-ΔadhE1+2 | ACE plasmid for the creation of adhE1 and adhE2 in-frame deletion in *C. autoethanogenum*. Plasmid contains a functional *C. acetobutylicum* pyrE as counter selectable marker |
| pMTL84151-Δaor2 | ACE plasmid for the creation of aor2 (CAETHG_0102) in-frame deletion in *C. autoethanogenum*. Plasmid contains functional *C. acetobutylicum* pyrE |
| pMTL007C-E2 | Clostridial expression vector for the ClosTron, containing a directed Group II intron with Erm RAM, flanked by FRT sites, ColE1, pCB102, $Cm^R/Tm^R$ |
| pMTL007C-E2::adhE1a-115s | ClosTron vector targeting Group II insertional knockout at the *C. autoethanogenum* adhE1 locus (upstream Ald domain of CAETHG_3747) |
| pMTL007C-E2::adhE1b-541s | ClosTron vector targeting Group II insertional knockout at the *C. autoethanogenum* adhE1 locus (downstream Adh domain of CAETHG_3747) |
| pMTL007C-E2::adhE2-662s | ClosTron vector targeting Group II insertional knockout at the *C. autoethanogenum* adhE2 locus (CAETHG_3748) |
| pMTL007C-E2::aor1-361s | ClosTron vector targeting Group II insertional knockout at the *C. autoethanogenum* aor1 locus (CAETHG_0092) |
| pMTL007C-E2::aor2-370s | ClosTron vector targeting Group II insertional knockout at the *C. autoethanogenum* aor2 locus (CAETHG_0102) |

ClosTron mutagenesis, and intron-retargeting tools generally, represents one of the most widely used clostridial mutagens. It employs a mobile group II intron that disrupts targeted genes by insertion (Heap, *J Microbiol Meth,* 80: 49-55, 2010; Heap, *J Microbiol Meth,* 70: 452-464, 2007). Here, it is shown that ClosTron can be successfully applied to an acetogen, and in particular *C. autoethanogenum* through the isolation of stable KO strains in genes adhE1, adhE2, aor1 and aor2.

For the construction of plasmid 'pMTL83151-PacsA', the promoter region of acsA (CAETHG_1621) of *C. autoethanogenum* was amplified using oligonucleotides 'PacsA-NotI-F' and 'PacsA-NdeI-R' followed by cloning into plasmid pMTL83151 (Heap, *J Microbiol Meth,* 78: 79-85, 2009) using restriction sites NotI and NdeI. To construct the aor1 expression plasmid, 'pMTL83151-PacsA-aor1', aor1 was subjected to two rounds of splice-overlapping extension (SOE-PCR) (Warrens, *Gene,* 186: 29-35, 1997) using primers to remove two interfering NdeI sites before cloning using restriction sites NdeI and KpnI. At both interfering sites (nucleotide 975 and 1284), nucleotides 'CAT' were mutated to 'CTT' while retaining the same amino acids. For the construction of ClosTron retargeting plasmids, the appropriate intron targeting regions within adhE1, adhE2, aor1 and aor2 were generated in silico from the ClosTron website using the Perutka algorithm (Perutka, *J Molec Biol,* 336: 421-439, 2004). DNA 2.0 Inc. then synthesized the 344 bp intron targeting region and cloned it into ClosTron vector pMTL007C-E2 (Heap, *J Microbiol Meth,* 80: 49-55, 2010) using restriction sites HindIII and BsrGI, resulting in plasmids 'pMTL007C-E2::adhE1a_115s' (targeting upstream Ald domain of adhE1), 'pMTL007C-E2::adhE1b_541s' (targeting downstream Adh domain of adhE1), 'pMTL007C-E2::adhE2_662s', 'pMTL007C-E2::aor1_361s' and 'pMTL007C-E2::aor2_370s'.

An allelic exchange plasmid was used for deletion of 227 bp of the C-terminus of *C. autoethanogenum* pyrE (CAETHG_1476), termed 'pMTL-AMH101'. Briefly, it contains a heterologous pyrE (cac_0027) from *C. acetobutylicum* ATCC 824 (to be employed as a counter selectable marker) and comprises a 303 bp short homology arm (SHA) and a 1219 bp great homology arm (GHA), with lacZα in between, as the allelic-exchange cassette. The in-frame deletion (IFD) allelic-exchange cassettes of *C. autoethanogenum* adhE1, adhE1+2, and aor2 consists of two homology arms of similar lengths (518-580 bp), and assembled using SOE-PCR and oligonucleotides. All the IFD cassettes retained only the start and stop codons of the target loci without affecting the 5'-untranslated region (UTR) and 3'-UTR. Following SOE-PCR, the IFD cassettes were digested with SacII and AscI and cloned into plasmid pMTL-AMH101 to generate plasmids 'pMTL84151-ΔadhE1', 'pMTL84151-ΔadhE1+2', and 'pMTL84151-Δaor2'. For the restoration of pyrE, a plasmid called pMTL-AMH102, which consists of a pyrE repair allelic exchange cassette with a 526 bp SHA and 1213 bp GHA, was employed.

1.4 Plasmid Transfer into *C. autoethanogenum*

Plasmids were transformed into *E. coli* donor strain CA434 (HB101 containing the conjugative plasmid R702) and then transferred into *C. autoethanogenum* via conjugation using previously established methods (Mock, *J Bacteriol*, 197: 2965-2980, 2015; Purdy, *Molec Microbiol*, 46: 439-452, 2002; Williams, *J Gen Microbiol*, 136: 819-826, 1990). Thiamphenicol (7.5 µg/mL) was used to select for catP-based plasmids. Trimethoprim (10 µg/mL) was used to counter select against *E. coli* CA434 after conjugation. For the validation of plasmid complementation strains, plasmids were isolated from *C. autoethanogenum* transconjugants and subsequently transformed into *E. coli* cells, before restriction digest analysis was carried out on the 'rescued' plasmids. The 16s rRNA gene was also amplified from the genomic DNA of transconjugants using oligonucleotides 'univ-0027-F' and 'univ-1492-R', followed by Sanger sequenced for verification purposes.

1.5 Construction of *C. autoethanogenum* ClosTron Strains

Figure 2:
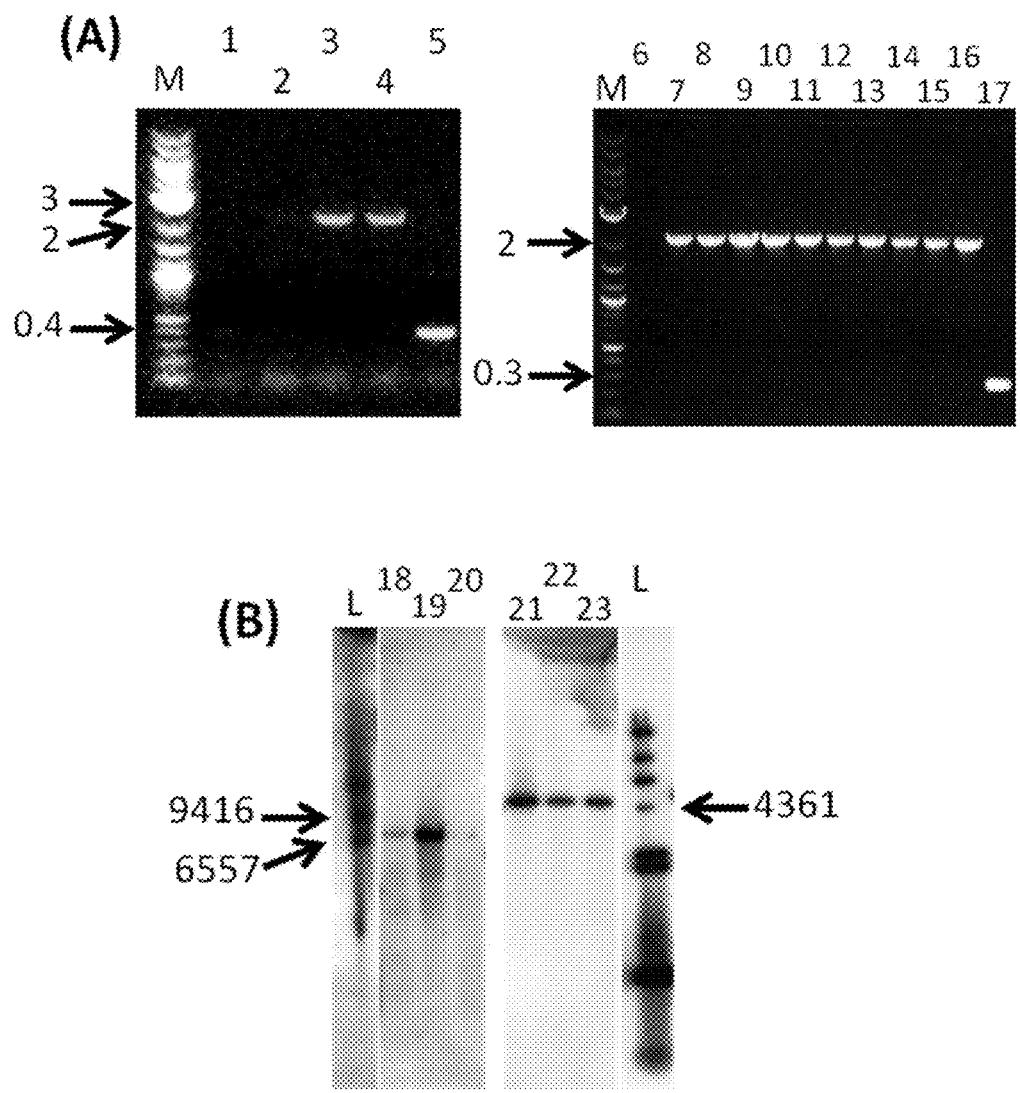
FIG. 2 is a set of gel images showing screening and validation of aor1 and aor2 KO strains. (A) Gel electrophoresis of PCR using exon-spanning primers; Lanes 3 & 4=aor1 KO strains; Lanes 7-16=aor2 KO strains; Lanes 1 & 6=Non-template controls; Lanes 5 & 17=WT controls; M=NEB 2-log DNA ladder in kb; (B) Southern Blot analysis of HindIII digested genomic DNA of aor1 KO strains (lanes 18-20), and aor2 KO strains (lanes 21-23); L=Promega Lambda DNA/HindIII marker in bp.
Figure 3:
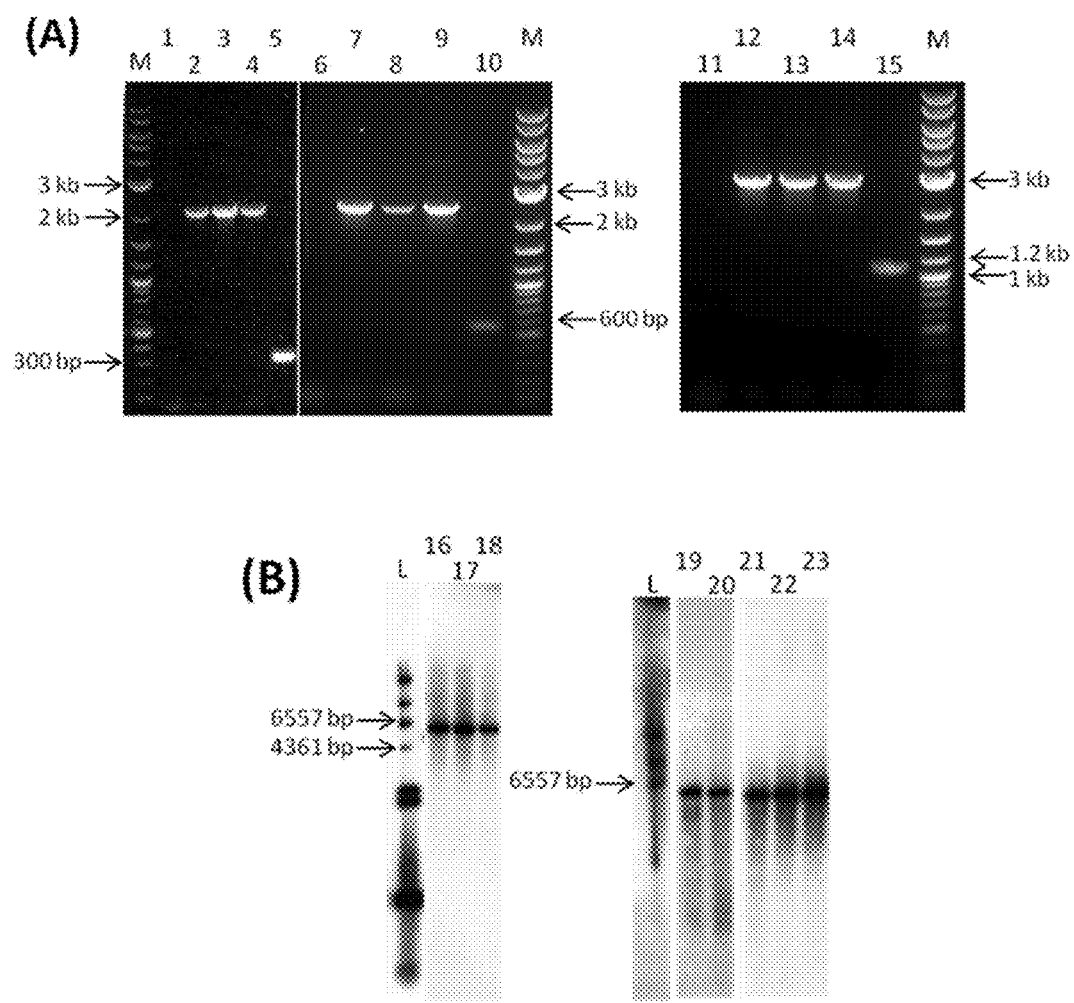
FIG. 3 is a set of gel images showing screening and validation of adhE1a, adhE1b, and adhE2 KO strains. (A) Gel electrophoresis of PCR using exon-spanning primers; Lanes 2-4=adhE1a KO strains; Lanes 7-9=adhE1b KO strains; Lanes 12-14=adhE2 KO strains; Lanes 1, 6, & 11=Non-template controls; Lanes 5, 10 & 15=WT controls; M=NEB 2-log DNA ladder; (B) Southern Blot analysis of HindIII digested genomic DNA of adhE1a KO strains (lanes 16-18), adhE1b KO strains (lanes 19 & 20), and adhE2 KO strains (lanes 21-23). L=Promega Lambda DNA/HindIII marker.

Following conjugation of ClosTron retargeting plasmids into *C. autoethanogenum*, thiamphenicol and trimethoprim resistant colonies were transferred onto solid YTF medium supplemented with 6 µg/mL clarithromycin to select for Intron insertion in target loci, and repeatedly streaked onto the same selective medium until plasmid loss was demonstrated as evident in the loss in ability to grow on medium supplemented with thiamphenicol. Genomic DNA was extracted from the clarithromycin resistant colonies and subjected to PCR screen using locus-specific flanking primers to identify clones that produced an amplicon that is 1.8 kb larger than WT control (indicative of ClosTron insertion at specified DNA locus) (FIG. 2 and FIG. 3). Sanger sequencing of the ClosTron amplicons was performed to validate the location of ClosTron insertion. As final verification, Southern Blot analysis was performed using a digoxigenin (DIG) High-Prime DNA labelling and detection kit (Roche) as instructed by the manufacturer to ensure that only one ClosTron insertion had occurred in each mutant (FIG. 2 and FIG. 3).

1.6 Allelic-Exchange Procedure 1.6.1 Creation of ΔpyrE Strain

ClosTron mutagenesis is fast and reproducible but it has some limitations. Most notably, intron insertion can have polar effects on downstream genes. Here, an allelic exchange method for *C. autoethanogenum* capable of making IFD was developed based on the use of a pseudo-suicide vector and a plasmid-encoded counter selection marker composed of a orotate phosphoribosyltransferase (pyrE) gene of *Clostridium acetobutylicum*. This is the equivalent approach to that taken in *Clostridium difficile* (Ng, Expending the repertoire of gene tools for precise manipulation of the *Clostridium difficile* genome, *PLOS One*, 8, 2013) and *C. acetobutylicum* (Ehsaan, *Biotechnol Biofuels*, 9: 1-20, 2016) where single crossover, chromosomal integrants of the pseudo-suicide, knock-out plasmid are detected on the basis of faster growth (larger colonies) on media supplemented with thiamphenicol. Pseudo-suicide plasmids make use of replication-defective plasmids (in this case the replicon of plasmid pMTL84151) which are consequently poorly segregated between daughter cells, limiting the growth of the cell population in the presence of antibiotic. Single crossover integrants, therefore, have a growth advantage in and can be used to select double crossover, plasmid excision derivatives by plating on the counter selection agent, 5-fluoroorotic acid (FOA). The latter is metabolised into the highly toxic compound 5-fluorouracil (FU) through the action of the plasmid-encoded PyrE enzyme. Only those cells that lose the pyrE gene following plasmid excision can survive. Excision events result in cells carrying either the original WT allele, or the desired mutant IFD allele. The two populations may be distinguished by appropriate PCR screening.

In order for pyrE to be used as a counter selection marker, the host must be a pyrE negative strain. Such hosts are relatively easily made using Allele-Coupled Exchange (ACE) (Heap, *Nucleic Acids Res*, 40: e59, 2012). Accordingly, an ACE vector equivalent to pMTL-YN18 (Ng, Expending the repertoire of gene tools for precise manipulation of the *Clostridium difficile* genome, *PLOS One*, 8, 2013) was made and used to generate a *C. autoethanogenum* derivative lacking the 3'-end (227 bp) of native pyrE gene (CAETHG_1476). The gene aor1 was first inactivated using ClosTron mutagenesis in this ΔpyrE strain, before IFD of aor2 was undertaken by allelic exchange using the pyrE-based KO vector (pMTL84151-Δaor2) and counter selection using FOA. Following creation of an aor1+2 KO strain, the mutant pyrE allele was restored to WT (uracil prototrophy) using a specially constructed ACE correction vector, analogous to pMTL-YN1 of *C. difficile* (Ng, Expending the repertoire of gene tools for precise manipulation of the *Clostridium difficile* genome, *PLOS One*, 8, 2013).

Figure 4:
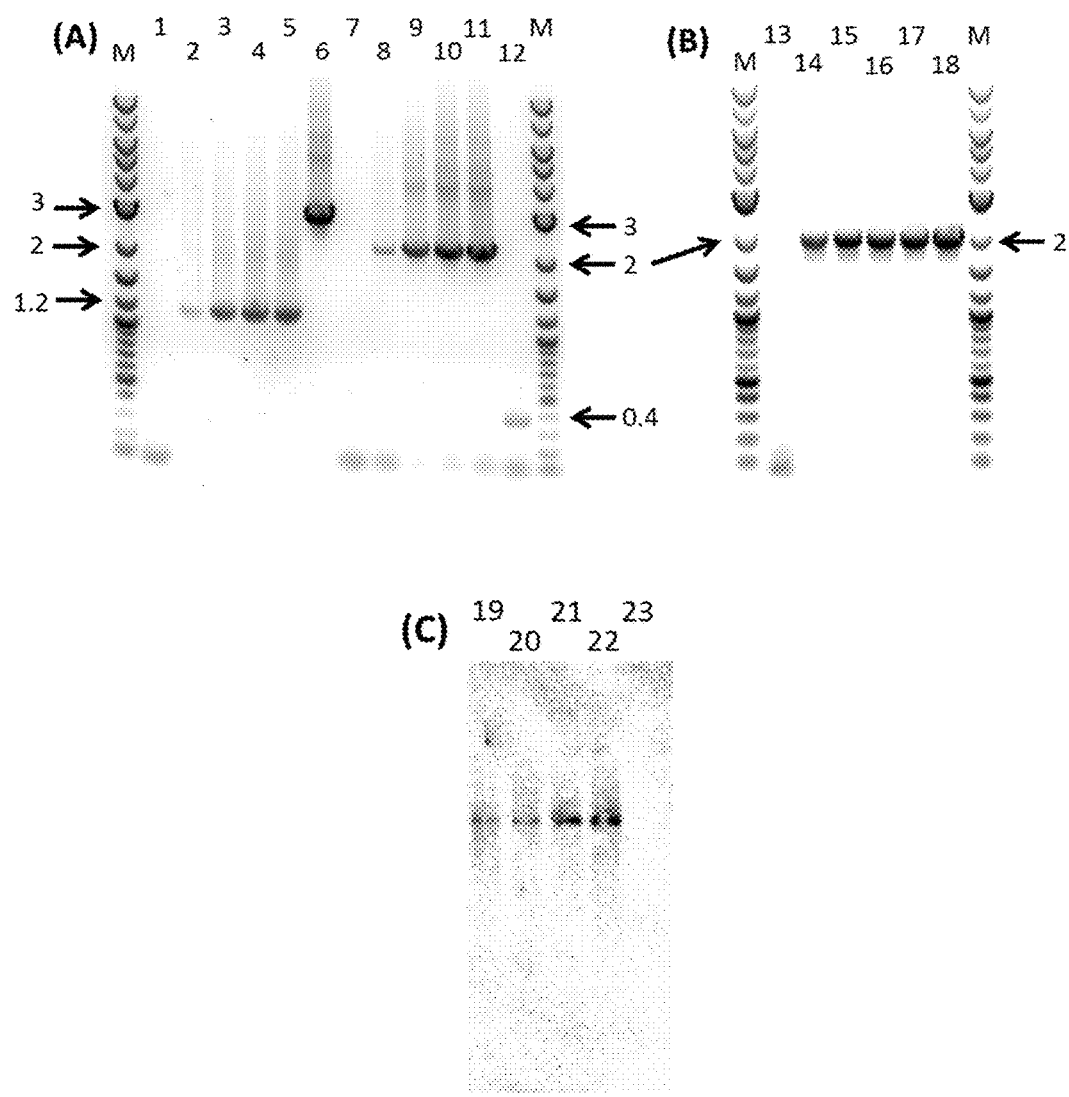
FIG. 4 is a set of gel images showing validation of aor double KO strain with restored pyrE. (A) PCR screening of Δaor2 and aor1 KO strain; (B) PCR screening of uracil autotrophic aor double KO strain for restored pyrE allele; (C) Southern Blot analysis of aor1 KO strain. M=NEB 2-log DNA ladder; 1-6=aor2-seq-F and aor2-seq-R primer pair; 7-12=aor1-559s-F and aor1-559s-R primer pair; 13-18=ACE-pyrE-F and ACE-pyrE-R primer pair; 1, 7 and 13=Non-template controls; 6, 12, 18 and 23=*C. autoetha-*

The procedure adopted was as previously described (Heap, *Nucleic Acids Res*, 40: e59, 2012). For the construction of ΔpyrE strain, which serves as a host for further IFD of adhE1, adhE1+2, and aor2 using pyrE as a positive and negative selectable marker, the plasmid pMTL84151-ΔpyrE was transformed into *C. autoethanogenum* via conjugation. The transconjugants were restreaked on YTF solid medium supplemented with thiamphenicol and trimethoprim to enrich and identify fast-growing single-crossover integrant clones. Genomic DNA was isolated and subjected to PCR analysis using two different primers (ACE-plasmid-F and ACE-plasmid-R) that anneal to plasmid specific sequences together with the appropriate locus-specific flanking primers. The presence of a DNA fragment indicated that the clones were indeed single-crossover integrants, while the size was indicative of at which homology arm the recombination event had occurred. PCR verified single-crossover integrants were inoculated into CaGM liquid medium supplemented with 10 g/L fructose and thiamphenicol and allowed to grow for 2 days inside anaerobic workstation, before they were serially diluted and plated. To facilitate the screening of rare second recombination events, the CaGM solid medium had 1 g/L yeast extract replaced with 1 g/L casein acid hydrolysate, and supplemented with 1.5 mg/mL fluoroorotic acid (FOA) and 5 µg/mL uracil. Incubation at 37° C. was carried out inside anaerobic workstation and FOA-resistant colonies that emerged within 2-3 days were restreaked onto the same selective medium before PCR screen using locus-specific flanking primers was performed to distinguish double-crossover recombinant clones from wild-type revertant clones. Sanger sequencing was employed to confirm the expected genotypes (FIG. 4).

1.6.2 Creation of ΔadhE1, ΔadhE1mut, and ΔadhE1+2 Strains

To explore the consequences of the deletion of both domains of adhE1, as well as adhE1+adhE2, appropriate in-frame deletion mutants of C. autoethanogenum were sought using pyrE-directed allelic exchange. In a first attempt of creating a ΔadhE1 strain, the strain ΔadhE1mut was obtained. PCR screen and Sanger sequencing of this strain revealed that the adhE1 of C. autoethanogenum was deleted, as well as an unintended deletion of 84 bp in the promoter region of adhE2 (FIG. 5). Examination of this promoter region in the WT sequence revealed the presence of two 9 bp repeats flanking the 84 bp deletion (FIG. 5). The 84 bp sequence comprises a putative terminator and the −10 and −35 box of the adhE2 promoter. A second attempt at generating a 'clean' IFD strain of adhE1 without the unintended 84 bp deletion was successful and yielded strain ΔadhE1 (FIG. 5). However, this strain persistently retained the plasmids used to generate the IFD despite repeated attempts to cure the strain of these plasmids. The creation of an adhE1 and adhE2 double IFD strain, ΔadhE1+2, was confirmed by PCR screen (FIG. 5) and Sanger sequencing that showed that both genes were successfully deleted without complications in the 5'-UTR of adhE1 and 3-'UTR of adhE2. After IFD no thiamphenicol sensitive clones of strain ΔadhE1+2 could be obtained. The ΔadhE1 and ΔadhE1+2 strains were not further characterized due to the retention of plasmids used to generate the IFD strains, which rendered them genetically unstable.

After the loss of plasmid was demonstrated by the loss of thiamphenicol resistance, the ΔpyrE strain could serve as a host for the recipient of plasmids pMTL84151-ΔadhE1, and pMTL84151-ΔadhE1+2 via conjugation for the construction of ΔadhE1 and ΔadhE1+2 strains, respectively. Single-crossover integrants and double-crossover FOA-resistant, uracil auxotrophic clones were obtained for both targets (same method as the ΔpyrE strain above). In the first attempt, Sanger sequencing revealed that in addition to the IFD of adhE1, an unintended 84 bp deletion had occurred in the promoter region of adhE2. Termed 'ΔadhE1mut', this strain also had the plasmid loss demonstrated by loss of thiamphenicol resistance. A second attempt at generating a 'clean' 'ΔadhE1' strain without the unintended 84 bp deletion was successful but repeated attempts to lose the plasmid (shown by persistent thiamphenicol resistance) was unsuccessful. For ΔadhE1+2 strain, Sanger sequencing revealed successful deletion of adhE1 and adhE2 without complications in the 5'-UTR of adhE1 and 3'-UTR of adhE2. However, repeated restreaking was unable to isolate thiamphenicol sensitive colonies for this strain.

1.6.3 Creation of Aor1+2 Double KO Strain

For the construction of the aor1+2 double knock-out strain (herein termed 'aor1+2 KO'), the aor1 locus was first inactivated using ClosTron plasmid pMTL007C-E2::aor1_361s in a ΔpyrE strain. Following the loss of plasmid, the IFD plasmid pMTL84151-Δaor2 was transformed and the isolation of single-crossover integrant and double-crossover recombinant clones were carried out as described above. These aor1 and aor2 double KO but uracil auxotrophic clones were transformed with plasmid pMTL-AMH102 to restore uracil prototrophy. Fast-growing thiamphenicol-resistant colonies were plated onto CaGM solid medium supplemented with 10 g/L fructose but had 1 g/L yeast extract replaced with 1 g/L casein acid hydrolysate without uracil supplementation. As final validation, PCR screen followed by Sanger sequencing was carried out using flanking primers to verify ClosTron insertion event in aor1, IFD of aor2 and restoration of pyrE. Plasmid loss in the form of thiamphenicol sensitivity was further demonstrated.

1.7 Harvest of Cells for Gene Expression Analysis

C. autoethanogenum recombinant strains were cultivated in triplicates of 500 mL pressure plus laboratory bottles (Duran), each containing 200 mL CaGM supplemented with 10 g/L fructose. For strains ΔpyrE and ΔadhE1mut, 10 μg/mL uracil was supplemented. In order to maintain plasmids in C. autoethanogenum harbouring plasmid pMTL83151-PacsA and pMTL83151-PacsA-aor1, 7.5 μg/mL of thiamphenicol was supplemented. Approximately 12 OD600 worth of cells were harvested at various growth phases by centrifugation at 4° C. at 3,220×g for 10 minutes. Supernatant was removed and the cell pellet was resuspended in 1 mL RNAlater Stabilization Solution (Ambion) by pipetting. After overnight incubation at 4° C., the cell suspension was centrifuged at 3,220×g at 4° C. for 10 minutes and supernatant discarded before storage at −80° C. until RNA extraction.

1.8 Total RNA Extraction and cDNA Synthesis

Following the addition of 1.5 mL cold TRIzol (Ambion), the thawed cell pellet was transferred into pre-chilled 2 mL microfuge tubes containing 1 g of dnature 0.1 mm diameter Zirconia/Silica beads (dnature Ltd). Cell disruption was performed in 3 cycles of 1 minute bead beating using Mini Beadbeater-16 (dnature Ltd), with 1 minute chilling on ice in between the cycles. Following 1 minute of 4° C. centrifugation at 20,238×g, the supernatant was harvested and 100 μL of chloroform was added, vortexed for 20 seconds and then incubated at room temperature for 15 minutes with occasional mixing. After the centrifugation at 20,238×g (4° C.) for 15 minutes, the aqueous phase was collected and 0.7 volume of isopropanol was added. The samples were incubated at room temperature for 10 minutes before centrifugation at 20,238×g (4° C.) for 10 minutes. Supernatant was removed and the DNA pellet was washed with 700 μL of ice-cold 70% (v/v) ethanol before another round of centrifugation 20,238×g (4° C.) for 10 minutes. Following the removal of supernatant, the RNA pellet was air-dried for 15 minutes before resuspension in 100 μL of RNase-free water and 1 μL of RNaseOUT (Invitrogen).

Genomic DNA was removed by the addition of TURBO DNase enzyme (Ambion) and 37° C. incubation for 30 minutes. The DNase-treated RNA was purified using RNA Clean and Concentrator Kit (Zymo Research) as per manufacturer's instructions and stored at −80° C. The concentration and purity of isolated RNA was analyzed spectrophotometrically using Nanodrop (Thermo Scientific). To ensure the absence of residual genomic DNA in the isolated RNA, 1 μL of each RNA samples was subjected to PCR analysis using primer pairs "adhE2-662s-F" and "adhE2-662s-R". The quality of RNA was examined using 2100 Bioanalyzer (Agilent Technologies) and RNA samples with RNA integrity number (RIN) greater than 7 were used for cDNA synthesis. Two μg of total RNA was used per 20 μL SuperScript III Reverse Transcriptase reactions (Invitrogen) and diluted 10-fold with RNase-free water prior to qPCR analysis.

1.9 Quantitative Reverse Transcriptase Polymerase Chain Reaction (qRT-PCR)

Primers and probe sets for target gene (adhE2) and housekeeping genes (gyrA and rho) (Table 5) were designed using the Custom TaqMan Assay Design Tool and purchased as Single-Tube Custom TaqMan Gene Expression Assays from Applied Biosystems. gyrA (CAETHG_2130; encodes DNA gyrase subunit A) and rho (CAETHG_2327; encodes transcriptional termination factor) were chosen as housekeeping genes because they exhibited the most stable gene expression levels in different carbon sources and stresses in closely related acetogen *C. ljungdahlii* DSM 13528 (Liu, *J Biosci Bioeng*, 116: 460-464, 2013). The amplification efficiencies of the TaqMan probes and primers were empirically determined to be between 94.2% and 99.7% ($R2 \geq 0.998$) by constructing a standard curve using serially diluted cDNA as template (data not shown).

TABLE 5

| Assay ID | Assay Name |
|---|---|
| AI89K3D | gyrA |
| AIAAZ86 | rho |
| AII1NGQ | adhE2 |

All qRT-PCR reactions were set up in 96-well Microseal PCR plates (Bio-Rad Laboratories) and performed in triplicates of 20 μL volume containing 1 μL diluted cDNA, 1 μL of 20× Custom TaqMan Gene Expression Assay, 10 μL of 2× TaqMan Gene Expression Master Mix (Applied Biosystems) and 8 μL nuclease-free water. Non-template controls (NTC) were included for each TaqMan probe and primer qRT-PCR master mixes. Each qRT-PCR runs comprised an initial denaturation and polymerase activation at 95° C. for 12 minutes, followed by 40 cycles of denaturation at 95° C. for 15 seconds and combined annealing and extension at 60° C. for 60 seconds. The CFX connect Real-Time PCR Detection System (Bio-Rad Laboratories) was employed to record the accumulation of signals in each well within the PCR plate, and the accompanying CFX Manager Software was used to perform normalized gene expression analysis.

1.10 Analytical Chemistry

Analysis of metabolites were performed using Varian ProStar HPLC system equipped with a RID (Refractive Index Detector) operated at 30° C. and a Aminex HPX-87H column (1300×7.8 mm, particle size 9 μm) (Bio-Rad Laboratories) kept at 30° C. Slightly acidified water was used (0.005 M $H_2SO_4$) as mobile phase with a flow rate of 0.5 mL/min. To remove proteins and other cell residues, samples were centrifuged at 20,238×g for 5 minutes and the supernatant was filtered with Spartan 13/0.2 RC filters. 10 μL of the supernatant was then injected into the HPLC for analyses.

1.11 Data Analysis and Presentations

Statistical analysis and graphically presented results were obtained using GraphPad Prism. Two-tailed, unpaired, parametric student's t-tests were employed for comparison of means.

1.12 Metabolic Engineering of Indirect Ethanol Pathway

Stoichiometric and thermodynamic analysis for acetogens such as *C. autoethanogenum* predicted that under autotrophic growth conditions ATP is limiting and very little ethanol could be formed without an initial ATP-generating step of acetate formation and then conversion to acetaldehyde via the action of AOR (Fast and Papoutsakis, 2012; Mock et al., 2015). The reduced ferredoxin required for AOR activity can be generated from the oxidation of CO (by carbon monoxide dehydrogenase) or $H_2$ (by an electron-bifurcating and NADP-dependent [FeFe]-hydrogenase (Wang et al., 2013)). The genome of *C. autoethanogenum* encodes two isoforms of aor: aor1 (CAETHG_0092) and aor2 (CAETHG_0102).

Autotrophic growth of single gene aor mutants: Serum bottle growth of the aor1 KO strain on CO was characterised by an extended lag phase (10 days), eventually achieving a cell density that was only half that of the WT (p-value<0.0001) (FIG. 6). The concentration of acetate made by the strain was, however, similar to that of the WT. In contrast, the aor1 KO strain made only 43% of the ethanol (p-value=0.019) and 23% of 2,3-butanediol (p-value<0.0001) (FIG. 6) produced by the WT. The aor1 KO strain synthesized 2.6 mM lactate, which was 11-fold higher than that of the WT level (p-value=0.001) (FIG. 6). In terms of growth rate and cell density, the aor2 KO strain behaved very similarly to the aor1 KO strain, although in this case the growth lag phase was extended to 25 days (FIG. 6). However, relative to the WT, the aor2 strain generated 170% more ethanol (p-value=0.009), 36% less acetate (p-value=0.0001), and similar levels of 2,3-butanediol and lactate (FIG. 6).

In an attempt to complement the aor1 KO strain, plasmid pMTL83151-PacsA-aor1 was transformed into this strain (FIG. 7). In terms of growth lag phase, the complemented strain behaved like the WT. The culture did reach a final cell density of OD600 of 1.28 compared to the 0.85 achieved by the aor1 KO strain (p-value=0.010) (FIG. 8). In contrast, the levels of ethanol and lactate produced were restored to WT levels in the complemented strain (FIG. 8).

Heterotrophic growth of single gene aor mutants: For evaluation of the impact of aor inactivation on heterotrophic growth, the aor1 KO and aor2 KO strains, together with the WT, were grown on fructose as the carbon source. As shown in FIG. 9, both aor KO strains reached similar cell densities, equivalent to the WT. Compared to the WT, the aor1 KO strain generated 21% more acetate (not statistically significant), 33% less ethanol (p-value=0.014) and 61% less 2,3-butanediol (p-value=0.018) (FIG. 9). In contrast, the aor2 KO strain synthesized amounts of acetate and 2,3-butanediol that were similar to the WT, but 47% more ethanol (p-value=0.003) (FIG. 9). HPLC results showed that all three strains completely exhausted the fructose provided and little or no lactate was produced (data not shown).

Different role of the two AOR isozymes: The two AOR isozymes are of the same length and they share 78% identity, but transcriptome data indicated that aor1 is expressed at 5-10× higher levels than aor2 during growth on CO (Mock et al., 2015) and both aor genes are expressed at higher levels during autotrophic growth as compared to heterotrophic growth. Consistent with the expression data, it was found that (i) inactivation of the higher expressed aor1 in *C. autoethanogenum* had a debilitating effect on the growth and formation of ethanol, and 2,3-butanediol in the presence of CO and (ii) growth of the aor1 KO strain was not significantly affected on fructose as the carbon source, but ethanol production was significantly reduced. In contrast, the inactivation of aor2 consistently increased ethanol production during growth on CO or fructose. One possible explanation for the contrasting phenotype is that AOR2 functions predominantly in the oxidation of acetaldehyde whereas AOR1 functions predominantly in the reduction of acetic acid. Alternatively, the inactivation of aor2 may reduce competition for access to substrate in the highly expressed and presumably more efficient AOR1, resulting in increased ethanol production. These results collectively suggest a contrasting role between aor1 and aor2 in ethanol production in *C. autoethanogenum*.

Both the aor1 KO and the aor2 KO strains exhibited a prolonged growth lag phase and reduced eventual cell density while growing on CO, indicating a deficiency in recycling the reduced ferredoxins generated from CO oxidation. An alternative avenue for the offload of reduced ferredoxin is the reaction involving pyruvate:ferredoxin oxidoreductase (PFOR) that converts acetyl-CoA and $CO_2$ to pyruvate, which may subsequently alter the production of pyruvate-derived products such as 2,3-butanediol and lactate (FIG. 1). The 11-fold higher levels of lactate production by the aor1 KO strain (but not by the aor2 KO strain) relative to WT showed that the production of lactate, rather than 2,3-butanediol, is the preferred route for achieving redox balance in the event of aor1 inactivation. From pyruvate, the generation of lactate involves only one enzyme (lactate dehydrogenase) whereas the biosynthesis of 2,3-butanediol involves three enzymes (acetolactate synthase, acetolactate decarboxylase and 2,3-butanediol dehydrogenase) (Köpke et al., 2014; Köpke et al., 2011) (FIG. 1). If 2,3-butanediol (a valuable platform chemical) is the preferred product, the lactate dehydrogenase (ldhA; CAETHG_1147) (Köpke et al., 2014) could be inactivated in an aor1 deficient strain.

The multiplicity of aor genes in *C. autoethanogenum* makes it however difficult to interpret the phenotype from single aor KO strain, as the unperturbed aor genes may compensate for any loss of activity associated with the inactivated gene. The aor1+2 double KO strain created in this example represents a unique strain that is completely devoid of functional AOR and has to rely on the direct reduction of acetyl-CoA into ethanol via acetaldehyde.

Autotrophic growth of double AOR mutant: During growth on pure CO, the aor1+2 double KO strain exhibited a prolonged lag phase, eventually achieving a cell density that was 69% lower than the WT (p-value<0.0001) and was only able to reduce the headspace pressure by 101 kPa over the course of the experiment, relative to a decrease of 163 kPa in WT control (FIG. 6). This retarded growth and poor gas consumption highlights the important role of AOR in supporting growth and utilization of CO.

In terms of metabolite production from CO, relative to the WT, the double KO strain produced 46% less ethanol (p-value=0.034), 38% less acetate (p-value<0.0001), 66% less 2,3-butanediol (p-value<0.0001) but 7.5-fold higher level of lactate (p-value<0.0001) (FIG. 6). These results indicate that while ethanol titre was halved as a result of AOR inactivation, the remaining half of the ethanol could still be synthesized from CO via the direct reduction of acetyl-CoA. It is worth mentioning that the aor1+2 double KO strain did not exhibit deficiencies of greater magnitudes in terms of growth and ethanol formation when compared to either the aor1 or the aor2 single KO strains. The phenotype of the aor1+2 double KO strain growing on CO best resemble that of the aor1 single KO strain, which provided further evidence aor1 (rather than aor2) is the main enzyme supporting growth on CO and ethanol biosynthesis.

On $H_2+CO_2$, the growth lag phase of the aor1+2 double KO strain slightly increased but was able to grow to similar cell density to the WT and reduced the same amount of headspace pressure as the WT control (FIG. 10). On a molar basis, only half the amount of reduced ferredoxin is generated from $H_2$ than CO (FIG. 1), which may lead to less redox imbalance and explain why the KO strain was able to grow largely unaffected on $H_2+CO_2$. Acetate production was not affected but the KO strain produced 9.2-fold less ethanol than WT (p-value<0.0001) (FIG. 10). No lactate or 2,3-butanediol was produced by either strain (data not shown).

The finding that a very high specific Aor activity was detected in the cell extract of $H_2+CO_2$ grown *C. autoethanogenum*, which was also 4-fold higher than CO-grown cell extract and 5.3-fold higher than fructose-cultivated cells (Mock et al., 2015), highlighted the significance of Aor in ethanol biosynthesis during $H_2+CO_2$ conditions. The results confirmed the prediction of Fast and Papoutsakis (2012) and Mock et al. (2015) that very little ethanol can be generated under the ATP-limiting $H_2+CO_2$ conditions without the action of Aor. Coincidentally, prominent acetogenic ethanol producers such as *C. ljungdahlii* (Köpke et al., 2010) and *C. carboxidivorans* (Bruant et al., 2010) possess Aor whereas non-ethanol producing acetogens such as *Acetobacterium woodii* (Poehlein et al., 2012) lack Aor.

Under ATP-sufficient heterotrophic growth on fructose, the growth, ethanol and 2,3-butanediol production of the aor1+2 double KO strain was not significantly affected (FIG. 9). In *Pyrococcus furiosus*, the deletion of its only Aor resulted in minimal ethanol production while growing on maltose (Basen et al., 2014).

1.13 Complete Disruption of Both Aor1 and Aor2 Abolishes Reduction of Carboxylic Acids into Alcohols Aor-harbouring acetogens such as *C. ljungdahlii* and *C. ragsdalei* have been shown to catalytically reduce a range of carboxylic acids, such as propionic acid, butyric acid, valeric and caproic acid into the corresponding primary alcohols using CO as electron donor (Isom et al., 2015; Perez et al., 2013). To investigate whether the Aor in *C. autoethanogenum* is capable of catalyzing such reactions, the WT and aor1+2 double KO strain were subjected to CO growth in the presence of supplemented 60 mM acetate, 40 mM propionate and 40 mM butyrate.

The supplementation of 60 mM acetate (a physiological metabolite) had a stimulatory effect on the CO growth of *C. autoethanogenum* as the lag phase was reduced from 5 days to 1 day (FIG. 11), but not the KO strain. Up to 31.3 mM acetate was consumed by the WT during early exponential phase but a net production of 79.1 mM acetate was recorded at stationary phase (FIG. 11). In the stationary phase, up to 70.8 mM ethanol was generated by the WT (FIG. 11). In contrast, the aor-deficient strain was not able to consume acetate during any of the growth stages and produced only 7.2 mM ethanol (FIG. 11). The reduction of acetic acid to aldehyde with reduced ferredoxin is thermodynamically very unfavourable under standard conditions ($\Delta Go'=35$ kJ/mol) (Thauer et al., 1977) because of the extremely low potential reaction ($Eo'=-580$ mV) (Loach, 1976). However, at physiological conditions with intracellular pH of 6.0 and 1000-fold higher intracellular acetate than acetaldehyde concentrations, the reaction is exergonic (Mock et al., 2015). The consumption of acetate with concomitant production of ethanol during exponential growth of *C. autoethanogenum* indicates that the acetogen readily catalyzes the reduction of acetic acid using CO as reductant.

Similar to the supplementation of acetate, the addition of non-physiological substrate propionate during CO cultivation reduced growth lag phase of WT from 5 days to 2 days (FIG. 12), whereas the growth lag phase of the aor1+2 double KO strain was not altered. An increase in cell density (OD600) from 0.61 (no supplementation) to 1.1 (propionate supplementation) and a reduction of headspace pressure to the same level of the WT was observed for the double KO strain (FIG. 12). Propionate concentrations remained unchanged and no 1-propanol was detected in cultures of double KO strain (FIG. 12). In contrast, in cultures of the WT strain 24.2 mM propionate was consumed and 20.9 mM 1-propanol produced during the exponential growth phase (FIG. 12).

In the case of butyrate supplementation in the presence of CO, the aor1+2 double KO strain grew to a similar OD600 as the WT and reduced headspace pressure to the same extent (FIG. 13). The KO strain produced 17% more acetate (p-value=0.019), 36% more 2,3-butanediol (not statistically significant), 2.8 mM lactate (whereas the WT produced none) but 44% less ethanol (p-value=0.016) than the WT. Consistent with the inability to metabolize acetate and propionate, the KO strain showed no consumption of the supplemented butyrate and produced no 1-butanol (FIG. 13). In contrast, in WT cultures 7.4 mM butyrate was consumed and 6.0 mM 1-butanol produced during the stationary growth phase (FIG. 13).

Taken together, these results demonstrated that the Aor of *C. autoethanogenum* is required for the reduction of carboxylic acids into their corresponding primary alcohols. To achieve a higher percentage of acid conversion, the headspace of the serum bottles would have to be regenerated with CO. The apparent wide substrate range of Aor in *C. autoethanogenum* is consistent with the finding that the crystal structure of Aor from *P. furiosus* identified a channel that is sufficiently spacious to accommodate a range of substrates including aliphatic and aromatic aldehydes (Chan et al., 1995). The Aor from *C. autoethanogenum* could be heterologously expressed in butyrate-producing acetogens such as *Clostridium drakei* (Gössner et al., 2008), *Clostridium scatologenes* (Küsel et al., 2000), *Eubacterium limosum* (Genthner et al., 1981) and *Oxobacter pfennigii* (Krumholz and Bryant, 1985) to generate 1-butanol.

1.14 Inactivation of adhE2 Reduces Ethanol Production Under Heterotrophic Conditions As part of the solventogenic pathway, the bi-functional AdhE is prevalent in many fermentative microorganisms. AdhE typically consists of an N-terminal acetylating Ald domain followed by a C-terminal Fe-type Adh domain (Extance et al., 2013; Membrillo-Hernandez et al., 2000). The key role of AdhE in alcohol formation has been demonstrated in *C. ljungdahlii* (Banerjee et al., 2014; Leang et al., 2013), *C. acetobutylicum* (Fontaine et al., 2002), *C. thermocellum* (Lo et al., 2015), *E. coli* (Membrillo-Hernandez et al., 2000), *Lactococcus lactis* (Arnau et al., 1998), *Geobacillus thermoglucosidasius* (Extance et al., 2013) and *Thermoanaerobacter ethanolicus* (Peng et al., 2008). The purified AdhE2 from *C. acetobutylicum* and AdhE from *T. ethanolicus* exhibited high Ald activity but low Adh activity (Fontaine et al., 2002; Peng et al., 2008), which may explain why many fermentative microorganisms possess multiple adh genes. Since deletion studies and the characterization of the separate AdhE domains indicate that the Ald and Adh domains are functionally autonomous (Arnau et al., 1998; Chen et al., 2004; Espinosa et al., 2001), the Ald domain and Adh domains of adhE1 in *C. autoethanogenum* was independently disrupted using ClosTron, generating the strains 'adhE1a KO' and 'adhE1b KO', respectively. For the 'adhE2' KO strain, only the Ald domain was targeted.

Growth of both the adhE1a KO and adhE1b KO strains on fructose was characterised by a slightly longer lag phase than the WT, but the cells eventually grew to a similar OD600 (FIG. 14). In contrast, the final OD600 of the adhE2 KO strain was 28% lower than the WT (p-value<0.0001) (FIG. 14). Even after 13 days of incubation, 0.92 g/L of fructose was detected in the adhE2 KO strain culture, whereas all the other strains completely exhausted the substrate prior to day 3 (data not shown). All three adhE KO strains reached peak acetate levels of 72.2-76.5 mM, which are 31-43% higher than the WT (p-values<0.05) (FIG. 14). When compared to the WT, both adhE1 KO strains produced similar amounts of ethanol but the adhE2 KO strain only generated 37% of the WT ethanol titres (p-value=0.0035) (FIG. 14). All three adhE KO strains produced less than half of the 2,3-butanediol recorded in the WT culture (p-values<0.05) (FIG. 14).

A genetically stable IFD strain of adhE1 (devoid of both Ald and Adh domains) that has lost the IFD plasmid was constructed in this example. However, an unintended deletion of 84 bp in the inter-genic region between adhE1 and adhE2 in *C. autoethanogenum* ΔadhE1mut strain inadvertently removed a transcriptional terminator and promoter of adhE2, resulting in strain ΔadhE1mut. In comparison to the parental strain (ΔpyrE control), growth of the ΔadhE1mut strain had a longer lag phase but both strains achieved a similar final cell density in the presence of fructose (FIG. 15). Both strains produced equivalent amounts of acetate (FIG. 15), ethanol (FIG. 15), and 2,3-butanediol (data not shown).

It is possible that the unperturbed promoter of adhE1 may mediate the expression of adhE2 as a result of this rearrangement. To test this hypothesis, adhE2 mRNA levels in the parental strain and the ΔadhE1mut strain were compared. Fructose-grown cells were harvested at early exponential phase, late exponential phase, and stationary phase. RNA was extracted and cDNA generated. Gene expression analysis showed that adhE2 transcript level of the parental strain was stable across all three time points (less than 3.2-fold difference) (FIG. 15). In contrast, adhE2 mRNA levels in the ΔadhE1mut strain exhibited large fluctuations with an initial decrease of 114-fold from early exponential growth phase to late exponential growth phase, followed by a 16-fold increase at the stationary growth phase (FIG. 15). Moreover, adhE2 transcript levels in the ΔadhE1mut strain were also significantly higher (15 to 1359-fold) than cells of the parental strain at all three sample time points (p-value<0.05) (FIG. 15). During autotrophic growth on $H_2+CO_2$, adhE1 is moderately expressed (61 FPKM) whereas adhE2 is barely expressed at all (0.4 FPKM) in *C. autoethanogenum* (Mock et al., 2015).

The finding that ethanol production from all three adhE1 inactivation strains (adhE1a KO, adhE1b KO and ΔadhE1 mut) was not impaired during heterotrophic growth contradicts the finding of Leang et al. (2013), who showed that the deletion of *C. ljungdahlii* adhE1 (but not adhE2) resulted in a strain that produced 6-fold less ethanol than the WT control. Furthermore, results in *C. autoethanogenum* demonstrated that adhE2 inactivation generated 63% lower ethanol concentration than the WT. One difference in growth experiment methodology is the use of 10 g/L fructose in this work but 5 g/L fructose in the study of Leang et al. (2013). RNA-sequencing experiments in both *C. autoethanogenum* (Marcellin et al., 2016) and *C. ljungdahlii* (Nagarajan et al., 2013; Tan et al., 2013) showed that adhE1 is transcribed at significantly higher levels when growing on fructose compared to autotrophic growth, which suggests an important for this gene under heterotrophic conditions.

A comparison of the amino acid (AA) sequences of AdhE1 and AdhE2 between *C. autoethanogenum* and *C. ljungdahlii* reveals that there are three substitutions in AdhE1 and eight substitutions in AdhE2. One of the AA changes in AdhE2 occurs in the NADH binding site of Adh domain. It is possible that one of these substitutions results in modification of substrate and cofactor specificities, as demonstrated by the change of cofactor from NADH to NADPH in the AdhE of *C. thermocellum* due to one AA change in the Fe-Adh domain (Brown et al., 2011). A change in cofactor specificity would be expected to have significant impact on electron and carbon flows because NADH is commonly used in catabolic reactions whereas NADPH is usually employed as reductant in anabolic processes (Alberts et al., 2002). Another possible explanation for the contradictory phenotypes is that *C. autoethanogenum* may possess other ethanologenic enzymes that compensate for the loss of AdhE activities during fructose growth.

1.15 Inactivation of Either adhE Consistently Increases Acetogenic Ethanol Production Conventional strategies that seek to enhance ethanol production commonly employ the introduction or overexpression of AdhE (Peng et al., 2008; Thapa et al., 2015; Yao and Mikkelsen, 2010). However, given the unique ATP-limiting conditions imposed during acetogenic growth and the presence of ethanologenic Aor in acetogens, such as *C. autoethanogenum*, it was hypothesized that the inactivation of adhE may divert carbon and reducing equivalents towards the ATP-yielding acetate formation. The acetic acid can be reduced to acetaldehyde (via Aor and reduced ferredoxins) and then ethanol via NAD(P)H-dependent Adh (FIG. 1).

During growth on pure CO, all three adhE KO strains (adhE1a, adhE1b, and adhE2) displayed significant growth deficiencies in the form of prolonged lag phase and 47-55% lower cell density than WT (p-values<0.01) (FIG. 16), which suggests inefficiency in recycling reducing equivalents. Despite the low biomass, all three adhE KO strains consistently generated 154-183% higher titres of ethanol while growing on CO. Specifically, the adhE1a KO strain produced 53.4 mM ethanol, 183% more than WT (p-value=0.0005). The adhE1b KO strain produced 171% more ethanol (not statistically significant) and the adhE2 KO strain produced 154% more ethanol than WT (p-value=0.021) (FIG. 16). These substantial improvements in ethanol production were partially offset by a reduction of 48-68% in 2,3-butanediol titres (p-values<0.004) (FIG. 16). Given the similarities in phenotypes between adhE1a KO strain and adhE1b KO strain, the position of ClosTron insertion within adhE1 (at Ald domain or Adh domain) played an insignificant role in the overall phenotype of the mutant.

In the $\Delta$adhE1mut strain, the enhanced adhE2 expression may compensate for the loss of AdhE1 activity. In agreement with this hypothesis, when compared to both adhE1a and adhE1b KO strains, the $\Delta$adhE1mut strain displayed a milder growth defect and generated similar amounts of acetate and 2,3-butanediol as the parental strain while growing on pure CO (FIG. 17). Consistent with the enhanced ethanol production phenotype under CO conditions, the $\Delta$adhE1mut strain generated 27% more ethanol than the parental strain (not statistically significant), which is less significant than the 171 to 183% increase recorded by both adhE1a and adhE1b KO strains.

The marked increase in ethanol production exhibited by the adhE inactivation strains while growing on CO is in agreement with the hypothesis that the ATP-efficient, indirect ethanol formation route employing Aor is more favourable for acetogenic ethanol biosynthesis. As further proof, the aor1+2 double KO strain generated only 54% of the ethanol attained by the WT under the same growth conditions. It has been hypothesized by Mock et al. (2015) that the CoA-linked acetaldehyde dehydrogenase activity measured in the $H_2+CO_2$-grown *C. autoethanogenum* physiologically only facilitate the reuse of the ethanol formed. During high ethanol concentration and low $H_2$ concentration, ethanol oxidation to acetyl-CoA is hypothesized to be coupled to the reduction of 2 $CO_2$ to acetate (Mock et al., 2015). In support of this notion, *C. autoethanogenum* WT growing on $H_2+CO_2$ transiently produced 10.3 mM ethanol during exponential growth but thereafter there was a steep decline to 1.8 mM during stationary phase. In addition to the two adhE genes, there are 3 other mono-functional ald genes (CAETHG_1819, 1830 & 3287) in the genome of *C. autoethanogenum*. Accordingly, the generation of a triple ald KO strain may further channel carbon and electrons towards acetate synthesis and ethanol formation via Aor.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Abrini, J., Naveau, H., Nyns, E. J., 1994. *Clostridium autoethanogenum*, sp. nov., an anaerobic bacterium that produces ethanol from carbon monoxide. Archives of Microbiology. 161, 345-351.
2. Alberts, B., Johnson, A., Lewis, J., Raff, M., Roberts, K., Walter, P., 2002. Catalysis and the use of energy by cells. Molecular Biology of The Cell. Garland Science, New York.

3. Arnau, J., Jorgensen, F., Madsen, S. M., Vrang, A., Israelsen, H., 1998. Cloning of the *Lactococcus lactis* adhE gene, encoding a multifunctional alcohol dehydrogenase, by complementation of a fermentative mutant of *Escherichia coli*. Journal of Bacteriology. 180, 3049-3055.

4. Banerjee, A., Leang, C., Ueki, T., Nevin, K. P., Lovley, D. R., 2014. Lactose-inducible system for metabolic engineering of *Clostridium ljungdahlii*. Applied and Environmental Microbiology. 80, 2410-2416.

5. Basen, M., Schut, G. J., Nguyen, D. M., Lipscomb, G. L., Benn, R. A., Prybol, C. J., Vaccaro, B. J., Poole, F. L., Kelly, R. M., Adams, M. W. W., 2014. Single gene insertion drives bioalcohol production by a thermophilic archaeon. PNAS USA. 111, 17618-17623.

6. Bertram, J., Dürre, P., 1989. Conjugal transfer and expression ofstreptococcal transposons in *Clostridium acetobutylicum*. Archives of Microbiology. 151, 551-557.

7. Brown, S. D., Guss, A. M., Karpinets, T. V., Parks, J. M., Smolin, N., Yang, S., Land, M. L., Klingeman, D. M., Bhandiwad, A., Rodriguez, M., Raman, B., Shao, X., Mielenz, J. R., Smith, J. C., Keller, M., Lynd, L. R., 2011. Mutant alcohol dehydrogenase leads to improved ethanol tolerance in *Clostridium thermocellum*. PNAS USA. 108, 13752-7.

8. Brown, S. D., Nagaraju, S., Utturkar, S., De Tissera, S., Segovia, S., Mitchell, W., Land, M. L., Dassanayake, A., Köpke, M., 2014. Comparison of single-molecule sequencing and hybrid approaches for finishing the genome of *Clostridium autoethanogenum* and analysis of CRISPR systems in industrial relevant Clostridia. Biotechnology for Biofuels. 7, 1-18.

9. Bruant, G., Levesque, M.-J., Peter, C., Guiot, S. R., Masson, L., 2010. Genomic analysis of carbon monoxide utilization and butanol production by *Clostridium carboxidivorans* strain P7. PloS one. 5, e13033.

10. Chan, M. K., Mukund, S., Kletzin, A., Adams, M. W., Rees, D. C., 1995. Structure of a hyperthermophilic tungstopterin enzyme, aldehyde ferredoxin oxidoreductase. Science. 267, 1463-1469.

11. Chen, M., Li, E., Stanley, S. L., Jr., 2004. Structural analysis of the acetaldehyde dehydrogenase activity of *Entamoeba histolytica* alcohol dehydrogenase 2 (EhADH2), a member of the ADHE enzyme family. Molecular and Biochemical Parasitology. 137, 201-5.

12. Ehsaan, M., Kuit, W., Zhang, Y., Cartman, S. T., Heap, J. T., Winzer, K., Minton, N. P., 2016. Mutant generation by allelic exchange and genome resequencing of the biobutanol organism *Clostridium acetobutylicum* ATCC 824. Biotechnology for Biofuels. 9, 1-20.

13. Espinosa, A., Yan, L., Zhang, Z., Foster, L., Clark, D., Li, E., Stanley, S. L., Jr., 2001. The bifunctional *Entamoeba histolytica* alcohol dehydrogenase 2 (EhADH2) protein is necessary for amebic growth and survival and requires an intact C-terminal domain for both alcohol dehydrogenase and acetaldehyde dehydrogenase activity. Journal of Biological Chemistry. 276, 20136-43.

14. Extance, J., Crennell, S. J., Eley, K., Cripps, R., Hough, D. W., Danson, M. J., 2013. Structure of a bifunctional alcohol dehydrogenase involved in bioethanol generation in *Geobacillus thermoglucosidasius*. Acta Crystallography. Section D, Biological Crystallography. vol. 69, United States, pp. 2104-15.

15. Fast, A. G., Papoutsakis, E. T., 2012. Stoichiometric and energetic analyses of non-photosynthetic CO2-fixation pathways to support synthetic biology strategies for production of fuels and chemicals. Current Opinion in Chemical Engineering. 1, 380-395.

16. Fontaine, L., Meynial-salles, I., Girbal, L., Yang, X., Croux, C., Soucaille, P., 2002. Molecular characterization and transcriptional analysis of adhE2, the gene encoding the NADH-dependent aldehyde/alcohol dehydrogenase responsible for butanol production in alcohologenic cultures of *Clostridium acetobutylicum* ATCC 824. Journal of Bacteriology. 184, 821-830.

17. Genthner, B. R. S., Davis, C. L., Bryant, M. P., 1981. Features of rumen and sewage sludge strains of *Eubacterium limosum*, a methanol-utilizing and H2-CO2-utilizing species. Applied and Environmental Microbiology. 42, 12-19.

18. Gössner, A. S., Picardal, F., Tanner, R. S., Drake, H. L., 2008. Carbon metabolism of the moderately acid-tolerant acetogen *Clostridium drakei* isolated from peat. FEMS Microbiology Letters. 287, 236-42.

19. Heap, J. T., Ehsaan, M., Cooksley, C. M., Ng, Y. K., Cartman, S. T., Winzer, K., Minton, N. P., 2012. Integration of DNA into bacterial chromosomes from plasmids without a counter-selection marker. Nucleic Acids Research. 40, e59.

20. Heap, J. T., Kuehne, S. a., Ehsaan, M., Cartman, S. T., Cooksley, C. M., Scott, J. C., Minton, N. P., 2010. The ClosTron: Mutagenesis in *Clostridium* refined and streamlined. Journal of Microbiological Methods. 80, 49-55.

21. Heap, J. T., Pennington, O. J., Cartman, S. T., Carter, G. P., Minton, N. P., 2007. The ClosTron: A universal gene knock-out system for the genus *Clostridium*. Journal of Microbiological Methods. 70, 452-464.

22. Heap, J. T., Pennington, O. J., Cartman, S. T., Minton, N. P., 2009. A modular system for *Clostridium* shuttle plasmids. Journal of Microbiological Methods. 78, 79-85.

23. Humphreys, C. M., McLean, S., Schatschneider, S., Millat, T., Henstra, A. M., Annan, F. J., Breitkopf, R., Pander, B., Piatek, P., Rowe, P., Wichlacz, A. T., Woods, C., Norman, R., Blom, J., Goesman, A., Hodgman, C., Barrett, D., Thomas, N. R., Winzer, K., Minton, N. P., 2015. Whole genome sequence and manual annotation of *Clostridium autoethanogenum*, an industrially relevant bacterium. BMC Genomics. 16, 1-10.

24. Isom, C. E., Nanny, M. A., Tanner, R. S., 2015. Improved conversion efficiencies for n-fatty acid reduction to primary alcohols by the solventogenic acetogen "*Clostridium ragsdalei*". Journal of Industrial Microbiology & Biotechnology. 42, 29-38.

25. Krumholz, L. R., Bryant, M. P., 1985. *Clostridium pfennigii* sp nov uses methoxyl groups of monobenzenoids and produces butyrate. International Journal of Systematic Bacteriology. 35, 454-456.

26. Köpke, M., Gerth, M. L., Maddock, D. J., Mueller, A. P., Liew, F., Simpson, S. D., Patrick, W. M., 2014. Reconstruction of an acetogenic 2,3-butanediol pathway involving a novel NADPH-dependent primary-secondary alcohol dehydrogenase. Applied and Environmental Microbiology. 80, 3394-3303.

27. Köpke, M., Held, C., Hujer, S., Liesegang, H., Wiezer, A., Wollherr, A., Ehrenreich, A., Liebl, W., Gottschalk, G., Dürre, P., 2010. *Clostridium ljungdahlii* represents a microbial production platform based on syngas. PNAS USA. 107, 13087-13092.

28. Köpke, M., Mihalcea, C., Liew, F. M., Tizard, J. H., Ali, M. S., Conolly, J. J., Al-Sinawi, B., Simpson, S. D., 2011. 2,3-butanediol production by acetogenic bacteria, an alternative route to chemical synthesis, using industrial waste gas. Applied and Environmental Microbiology. 77, 5467-5475.
29. Küsel, K., Dorsch, T., Acker, G., Stackebrandt, E., Drake, H. L., 2000. *Clostridium scatologenes* strain SL1 isolated as an acetogenic bacterium from acidic sediments. International Journal of Systematic and Evolutionary Microbiology. 50 Pt 2, 537-546.
30. Leang, C., Ueki, T., Nevin, K. P., Lovley, D. R., 2013. A genetic system for *Clostridium ljungdahlii*: A chassis for autotrophic production of biocommodities and a model homoacetogen. Applied and Environmental Microbiology. 79, 1102-1109.
31. Liu, J., Tan, Y., Yang, X., Chen, X., Li, F., 2013. Evaluation of *Clostridium ljungdahlii DSM* 13528 reference genes in gene expression studies by qRT-PCR. Journal of Bioscience and Bioengineering. 116, 460-464.
32. Lo, J., Zheng, T., Hon, S., Olson, D. G., Lynd, L. R., 2015. The bifunctional alcohol and aldehyde dehydrogenase gene, adhE, is necessary for ethanol production in *Clostridium thermocellum* and *Thermoanaerobacterium saccharolyticum*. Journal of Bacteriology. 197, 1386-93.
33. Loach, P. A., 1976. Oxidation-reduction potentials, absorbance bands and molar absorbance of compounds used in biochemical studies. In: Fasman, G. D., (Ed.), Handbook of biochemistry and molecular biology. vol. 1. CRC Press, Cleveland, pp. 122-130.
34. Marcellin, E., Behrendorff, J. B., Nagaraju, S., DeTissera, S., Segovia, S., Palfreyman, R., Daniell, J., Licona-Cassani, C., Quek, L.-e., Speight, R., Hodson, M. P., Simpson, S. D., Mitchell, W. P., Köpke, M., Nielsen, L. K., 2016. Low carbon fuels and commodity chemicals from waste gases—Systematic approach to understand energy metabolism in a model acetogen. Green Chemistry.
35. Membrillo-Hernandez, J., Echave, P., Cabiscol, E., Tamarit, J., Ros, J., Lin, E. C., 2000. Evolution of the adhE gene product of *Escherichia coli* from a functional reductase to a dehydrogenase. Genetic and biochemical studies of the mutant proteins. Journal of Biological Chemistry. 275, 33869-75.
36. Mock, J., Zheng, Y., Mueller, A. P., Ly, S., Tran, L., Segovia, S., Nagaraju, S., Köpke, M., Dürre, P., Thauer, R. K., 2015. Energy conservation associated with ethanol formation from H2 and CO2 in *Clostridium autoethanogenum* involving electron bifurcation. Journal of Bacteriology. 197, 2965-2980.
37. Nagaraj an, H., Sahin, M., Nogales, J., Latif, H., Lovley, D., Ebrahim, A., Zengler, K., 2013. Characterizing acetogenic metabolism using a genome-scale metabolic reconstruction of *Clostridium ljungdahlii*. Microbial Cell Factories. 12, 118.
38. Ng, Y. K., Ehsaan, M., Philip, S., Collery, M. M., Janoir, C., Collignon, A., Cartman, S. T., Minton, N. P., 2013. Expending the repertoire of gene tools for precise manipulation of the *Clostridium difficile* genome: Allelic exchange using pyrE alleles. Plos One. 8.
39. Peng, H., Wu, G. G., Shao, W. L., 2008. The aldehyde/alcohol dehydrogenase (AdhE) in relation to the ethanol formation in *Thermoanaerobacter ethanolicus* JW200. Anaerobe. 14, 125-127.
40. Perez, J. M., Richter, H., Loftus, S. E., Angenent, L. T., 2013. Biocatalytic reduction of short-chain carboxylic acids into their corresponding alcohols with syngas fermentation. Biotechnology and Bioeninineering. 110, 1066-77.
41. Perutka, J., Wang, W., Goerlitz, D., Lambowitz, A. M., 2004. Use of computer-designed group II introns to disrupt *Escherichia coli* DExH/D-box protein and DNA helicase genes. Journal of Molecular Biology. 336, 421-439.
42. Poehlein, A., Schmidt, S., Kaster, A. K., Goenrich, M., Vollmers, J., Thurmer, A., Bertsch, J., Schuchmann, K., Voigt, B., Hecker, M., Daniel, R., Thauer, R. K., Gottschalk, G., Müller, V., 2012. An ancient pathway combining carbon dioxide fixation with the generation and utilization of a sodium ion gradient for ATP synthesis. Plos One. 7.
43. Purdy, D., O'Keeffe, T. A. T., Elmore, M., Herbert, M., McLeod, A., Bokori-Brown, M., Ostrowski, A., Minton, N. P., 2002. Conjugative transfer of clostridial shuttle vectors from *Escherichia coli* to *Clostridium difficile* through circumvention of the restriction barrier. Molecular Microbiology. 46, 439-452.
44. Sambrook, J., Russell, D. W., 2001. Molecular cloning: A laboratory manual. Cold Spring Harbor Laboratory Press, New York.
45. Tan, Y., Liu, J. J., Chen, X. H., Zheng, H. J., Li, F. L., 2013. RNA-seq-based comparative transcriptome analysis of the syngas-utilizing bacterium *Clostridium ljungdahlii* DSM 13528 grown autotrophically and heterotrophically. Molecular Biosystems. 9, 2775-2784.
46. Thapa, L. P., Lee, S. J., Yang, X., Lee, J. H., Choi, H. S., Park, C., Kim, S. W., 2015. Improved bioethanol production from metabolic engineering of *Enterobacter aerogenes* ATCC 29007. Process Biochemistry.
47. Thauer, R. K., Jungermann, K., Decker, K., 1977. Energy conservation in chemotrophic anerobic bacteria. Bacteriological Reviews. 41, 100-180.
48. Utturkar, S. M., Klingeman, D. M., Bruno-Barcena, J. M., Chinn, M. S., Grunden, A. M., Köpke, M., Brown, S. D., 2015. Sequence data for *Clostridium autoethanogenum* using three generations of sequencing technologies. Scientific Data. 2, 1-9.
49. Wang, S., Huang, H., Kahnt, H. H., Mueller, A. P., Köpke, M., Thauer, R. K., 2013. NADP-specific electron-bifurcating [FeFe]-hydrogenase in a functional complex with formate dehydrogenase in *Clostridium autoethanogenum* grown on CO. Journal of Bacteriology. 195, 4373-4386.
50. Warrens, A. N., Jones, M. D., Lechlera, R. I., 1997. Splicing by overlap extension by PCR using asymmetric amplification: an improved technique for the generation of hybrid proteins of immunological interest. Gene. 186, 29-35.
51. Weisburg W G, Barns S M, Pelletier D A, Lane D J. 1991. 16S ribosomal DNA amplification for phylogenetic study. Journal of Bacteriology 173:697-703.
52. Williams, D. R., Young, D. I., Young, M., 1990. Conjugative plasmid transfer from *Escherichia coli* to *Clostridium acetobutylicum*. Journal of General Microbiology. 136, 819-826.
53. Yao, S., Mikkelsen, M. J., 2010. Identification and overexpression of a bifunctional aldehyde/alcohol dehydrogenase responsible for ethanol production in *Thermoanaerobacter mathranii*. Journal of Molecular Microbiology and Biotechnology. 19, 123-133.

The invention claimed is:
1. A non-naturally occurring bacterium having decreased or eliminated activity of an enzyme belonging to EC 1.2.7.5 compared to a parental bacterium, wherein the non-naturally occurring bacterium comprises at least one disruptive mutation in a gene encoding the enzyme that belongs to EC 1.2.7.5.

2. The non-naturally occurring bacterium of claim 1, wherein the enzyme belonging to EC 1.2.7.5 is aldehyde: ferredoxin oxidoreductase.

3. The non-naturally occurring bacterium of claim 1, wherein the non-naturally occurring bacterium further has decreased or eliminated activity of at least one enzyme belonging to EC 1.2.1.10 and/or EC 1.1.1.1 compared to the parental bacterium, wherein the non-naturally occurring bacterium comprises at least one disruptive mutation in a gene encoding the enzyme that belongs to EC 1.2.1.10 and/or EC 1.1.1.1.

4. The non-naturally occurring bacterium of claim 3, wherein the enzyme belonging to EC 1.2.1.10 and/or EC 1.1.1.1 is selected from the group consisting of bifunctional aldehyde/alcohol dehydrogenase, aldehyde dehydrogenase, and alcohol dehydrogenase.

5. The non-naturally occurring bacterium of claim 1, wherein the non-naturally occurring bacterium produces a product selected from the group consisting of acetyl-CoA, acetoacetyl-CoA, acetoacetate, acetone, isopropanol, 3-hydroxyisovaleryl-CoA, 3-hydroxyisovalerate, isobutylene, isoprene, 3-hydroxybutyryl-CoA, 3-hydroxybutyrate, 3-hydroxybutyrylaldehyde, 1,3-butanediol, 2-hydroxyisobutyryl-CoA, 2-hydroxyisobutyrate, pyruvate, acetolactate, acetoin, 2,3-butanediol and lactate.

6. The non-naturally occurring bacterium of claim 1, wherein the non-naturally occurring bacterium consumes a gaseous substrate comprising one or more of CO, $CO_2$, and $H_2$.

7. The non-naturally occurring bacterium of claim 1, wherein the parental bacterium is selected from the group consisting of *Alkalibaculum bacchi, Blautia product, Butyribacterium methylotrophicum, Chloroflexus aurantiacus, Clostridium aceticum, Clostridium acetobutylicum, Clostridium autoethanogenum, Clostridium botulinum, Clostridium carboxidivorans, Clostridium coskatii, Clostridium drakei, Clostridium formicoaceticum, Clostridium ljungdahlii, Clostridium ragsdalei, Desulfovibrio vulgaris, Eubacterium limosum, Geobacter sulfurreducens, Methylomicrobium alcaliphilum, Moorella thermoautrophica, Moorella thermoacetica, Rhodospirillum rubrum, Sporomusa ovata, Sporomusa silvacetica, Sporomusa sphaeroides, Thermanaerovibrio acidaminovorans, Thermanaerovibrio acidaminovorans, Thermoanaerobacter wiegelii, Thermodesulfovibrio yellowstonii, Thermodesulfovibrio yellowstonii,* and *Thermus thermophilus*.

8. A method of producing a product by culturing the non-naturally occurring bacterium of claim 1 in the presence of a gaseous substrate comprising one or more of CO, $CO_2$, and $H_2$.

9. The method of claim 8, wherein the enzyme belonging to EC 1.2.7.5 is aldehyde:ferredoxin oxidoreductase.

10. The method of claim 8, wherein the non-naturally occurring bacterium further has decreased or eliminated activity of at least one enzyme belonging to EC 1.2.1.10 and/or EC 1.1.1.1 compared to the parental bacterium, wherein the non-naturally occurring bacterium comprises at least one disruptive mutation in a gene encoding the enzyme that belongs to EC 1.2.1.10 and/or EC 1.1.1.1.

11. The method of claim 10, wherein the enzyme belonging to EC 1.2.1.10 and/or EC 1.1.1.1 is selected from the group consisting of bifunctional aldehyde/alcohol dehydrogenase, aldehyde dehydrogenase, and alcohol dehydrogenase.

12. The method of claim 8, wherein the product is an acetyl-CoA-derived product selected from the group consisting of acetyl-CoA, acetoacetyl-CoA, acetoacetate, acetone, isopropanol, 3-hydroxyisovaleryl-CoA, 3-hydroxyisovalerate, isobutylene, isoprene, 3-hydroxybutyryl-CoA, 3-hydroxybutyrate, 3-hydroxybutyrylaldehyde, 1,3-butanediol, 2-hydroxyisobutyryl-CoA, 2-hydroxyisobutyrate, pyruvate, acetolactate, acetoin, 2,3-butanediol and lactate.

13. The method of claim 8, wherein the parental bacterium is selected from the group consisting of *Alkalibaculum bacchi, Blautia product, Butyribacterium methylotrophicum, Chloroflexus aurantiacus, Clostridium aceticum, Clostridium acetobutylicum, Clostridium autoethanogenum, Clostridium botulinum, Clostridium carboxidivorans, Clostridium coskatii, Clostridium drakei, Clostridium formicoaceticum, Clostridium ljungdahlii, Clostridium ragsdalei, Desulfovibrio vulgaris, Eubacterium limosum, Geobacter sulfurreducens, Methylomicrobium alcaliphilum, Moorella thermoautrophica, Moorella thermoacetica, Rhodospirillum rubrum, Sporomusa ovata, Sporomusa silvacetica, Sporomusa sphaeroides, Thermanaerovibrio acidaminovorans, Thermanaerovibrio acidaminovorans, Thermoanaerobacter wiegelii, Thermodesulfovibrio yellowstonii, Thermodesulfovibrio yellowstonii,* and *Thermus thermophilus*.

\* \* \* \* \*